(12) United States Patent
Karathanasis et al.

(10) Patent No.: US 10,729,652 B2
(45) Date of Patent: Aug. 4, 2020

(54) MULTI-COMPONENT NANOCONSTRUCTS

(71) Applicant: CASE WESTERN RESERVE UNIVERSITY, Cleveland, OH (US)

(72) Inventors: Efstathios Karathanasis, Solon, OH (US); Watuthentrige Pubudu M. Peiris, Twinsburg, OH (US); Elizabeth Doolittle, Mount Vernon, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

(21) Appl. No.: 15/922,429

(22) Filed: Mar. 15, 2018

(65) Prior Publication Data

US 2018/0263910 A1  Sep. 20, 2018

Related U.S. Application Data

(60) Provisional application No. 62/471,765, filed on Mar. 15, 2017.

(51) Int. Cl.

| | |
|---|---|
| *A61K 9/14* | (2006.01) |
| *A61K 9/127* | (2006.01) |
| *A61K 33/26* | (2006.01) |
| *A61K 33/242* | (2019.01) |
| *A61K 47/69* | (2017.01) |
| *A61K 47/64* | (2017.01) |
| *A61K 9/00* | (2006.01) |
| *A61K 49/18* | (2006.01) |

(52) U.S. Cl.
CPC ............ *A61K 9/143* (2013.01); *A61K 9/0009* (2013.01); *A61K 9/0019* (2013.01); *A61K 9/1271* (2013.01); *A61K 9/146* (2013.01); *A61K 33/242* (2019.01); *A61K 33/26* (2013.01); *A61K 47/64* (2017.08); *A61K 47/6923* (2017.08); *A61K 49/1866* (2013.01); *Y10S 977/773* (2013.01); *Y10S 977/906* (2013.01); *Y10S 977/907* (2013.01)

(58) Field of Classification Search
None
See application file for complete search history.

(56) References Cited

U.S. PATENT DOCUMENTS

| | | | |
|---|---|---|---|
| 9,439,966 B2* | 9/2016 | Karathanasis | A61K 38/16 |
| 10,143,653 B2* | 12/2018 | Karathanasis | A61K 41/0057 |
| 2004/0077844 A1* | 4/2004 | Jacobson | B05D 1/00 530/391.5 |
| 2013/0197214 A1* | 8/2013 | Jacobson | B05D 1/00 536/121 |

(Continued)

OTHER PUBLICATIONS

PM Peiris et al. "Enhanced Delivery of Chemotherapy to Tumors Using a Multicomponent Nanochain with Radio-Frequency-Tunable Drug Release." ACS Nano, vol. 6 No. 5, 2012, pp. 4157-4168. (Year: 2012).*

(Continued)

*Primary Examiner* — Isaac Shomer
(74) *Attorney, Agent, or Firm* — Tarolli, Sundheim, Covell & Tummino LLP

(57) ABSTRACT

A multi-component nanoconstruct for use in diagnostic and therapeutic applications includes at least three nanoparticles linked together to form the nanochain. The nanoparticles are linked to form the nanochain by linking first linkers and/or second linkers disposed on separate nanoparticles.

22 Claims, 9 Drawing Sheets

Specification includes a Sequence Listing.

(56) References Cited

U.S. PATENT DOCUMENTS

2014/0248339 A1* 9/2014 Karathanasis ..... A61K 41/0009
                                                          424/450

OTHER PUBLICATIONS

PM Peiris et al. "Treatment of Invasive Brain Tumors Using a Chain-like Nanoparticle." Cancer Research, vol. 75(7), Apr. 1, 2015, pp. 1356-1365. (Year: 2015).*

VS Perera et al. "One-pot synthesis of nanochain particles for targeting brain tumors." Nanoscale, vol. 9, 2017, pp. 9659-9667, published Jun. 27, 2017. (Year: 2017).*

K-M Sung, DW Mosley, BR Peelle, S Zhang, JM Jacobson. "Synthesis of Monofunctionalized Gold Nanoparticles by Fmoc Solid-Phase Reactions." Journal of the American Chemical Society, vol. 126, 2004, pp. 5064-5065. (Year: 2004).*

PM Peiris, E Schmidt, M Calabrese, E Karathanasis. "Assembly of Linear Nano-Chains from Iron Oxide Nanospheres with Asymmetric Surface Chemistry." PLoS One, Jan. 2011, vol. 6, Issue 1, e15927, pp. 1-9. (Year: 2011).*

* cited by examiner

Figs. 1A-C

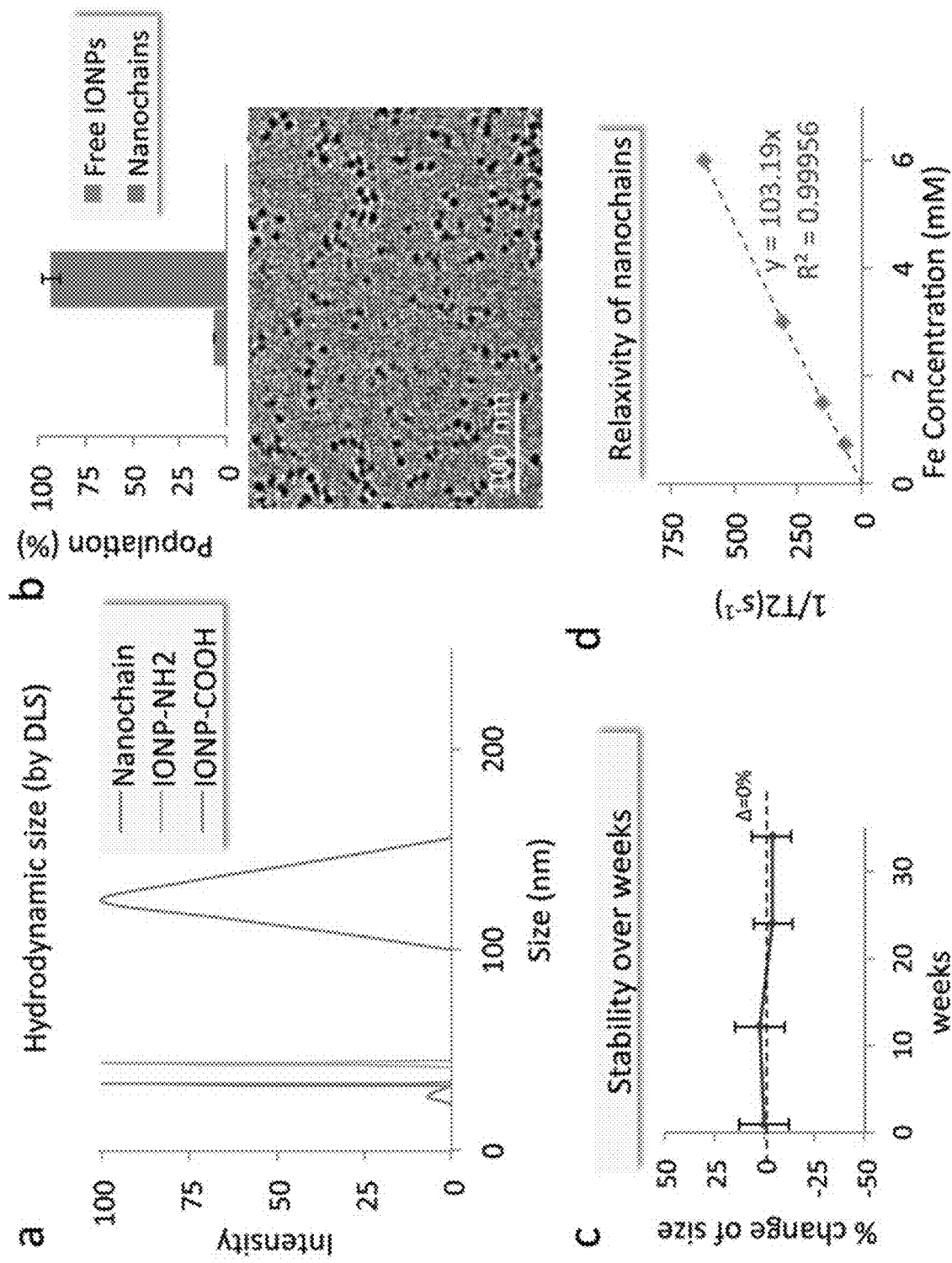
Figs. 3A-D

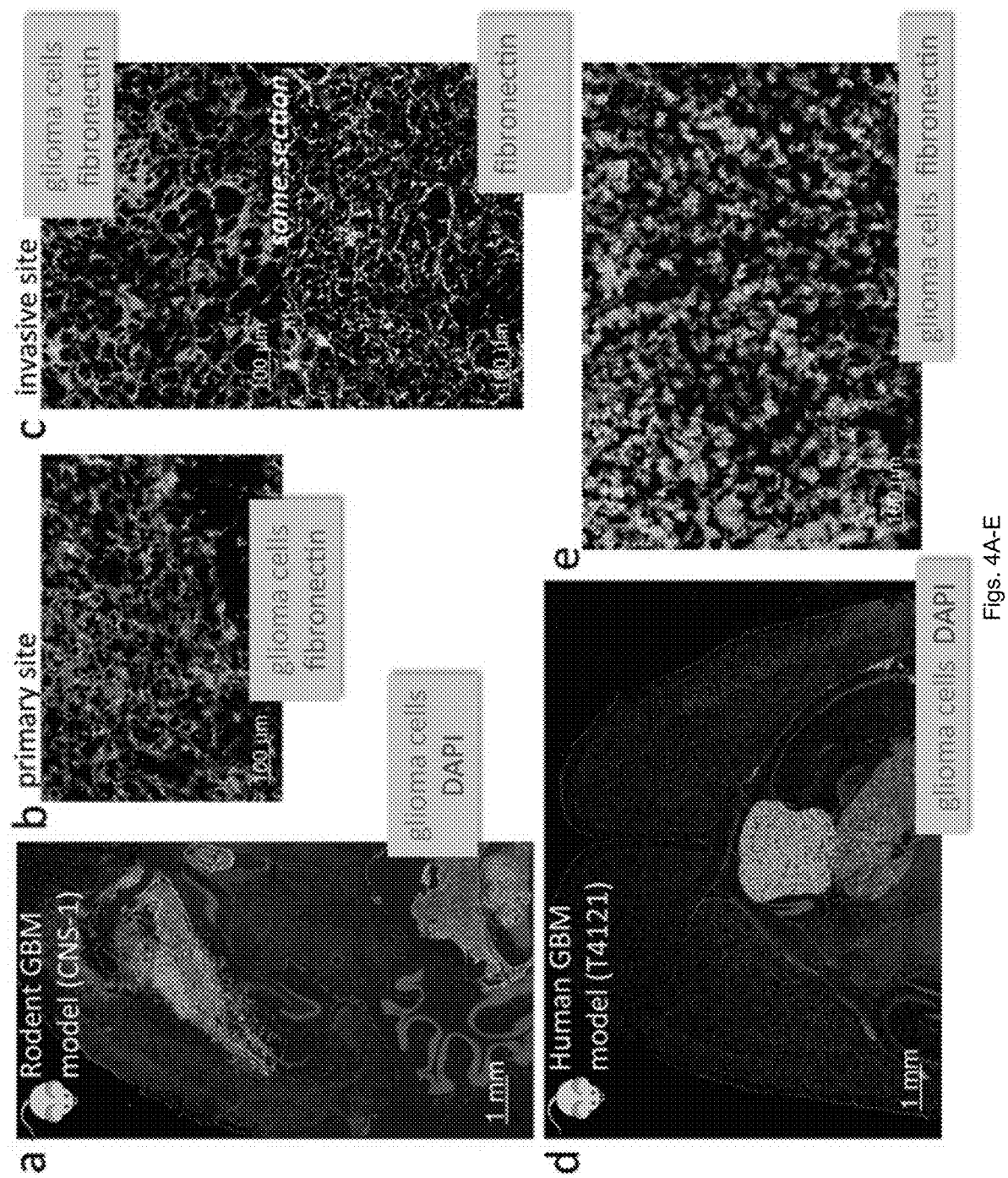
Figs. 4A-E

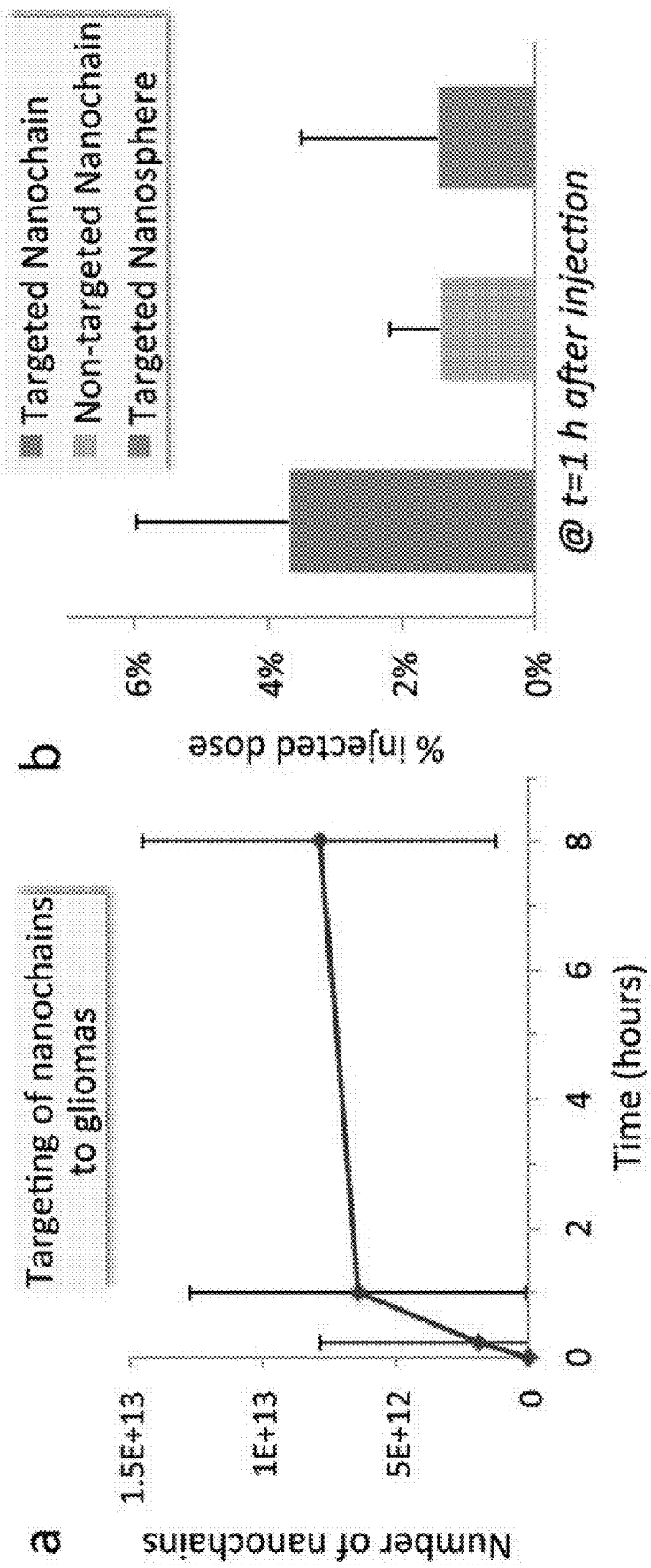
Figs. 5A-B

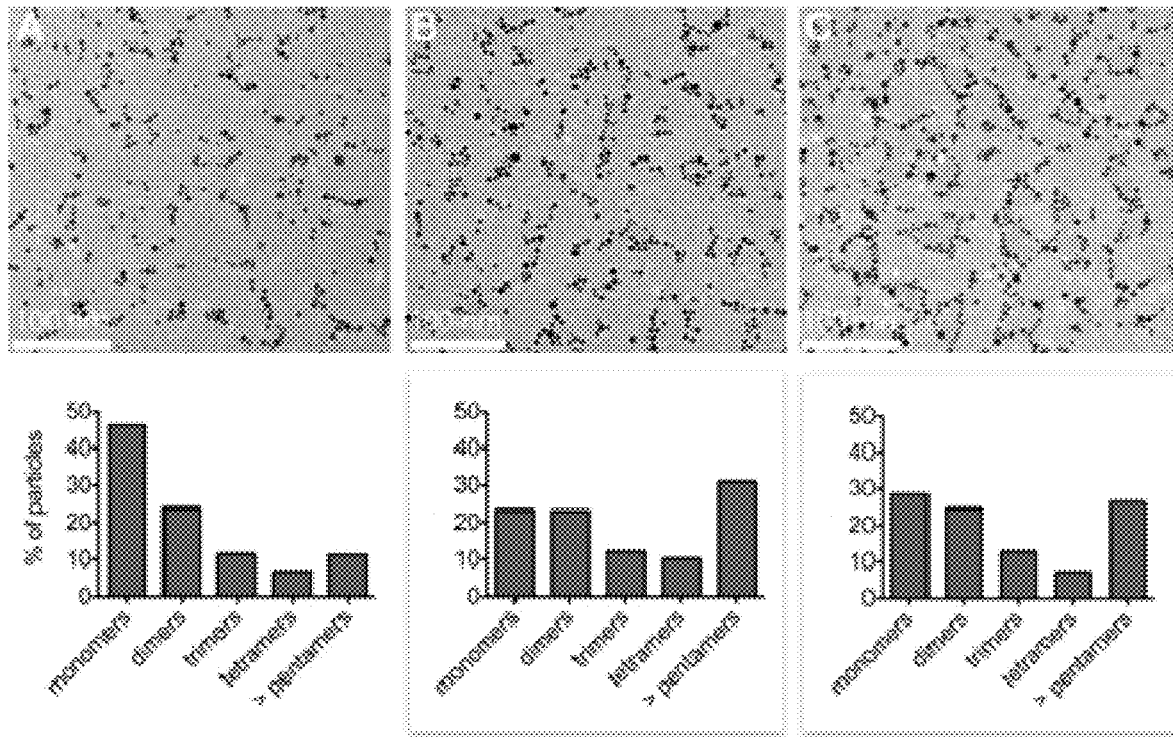
Figs. 8A-C
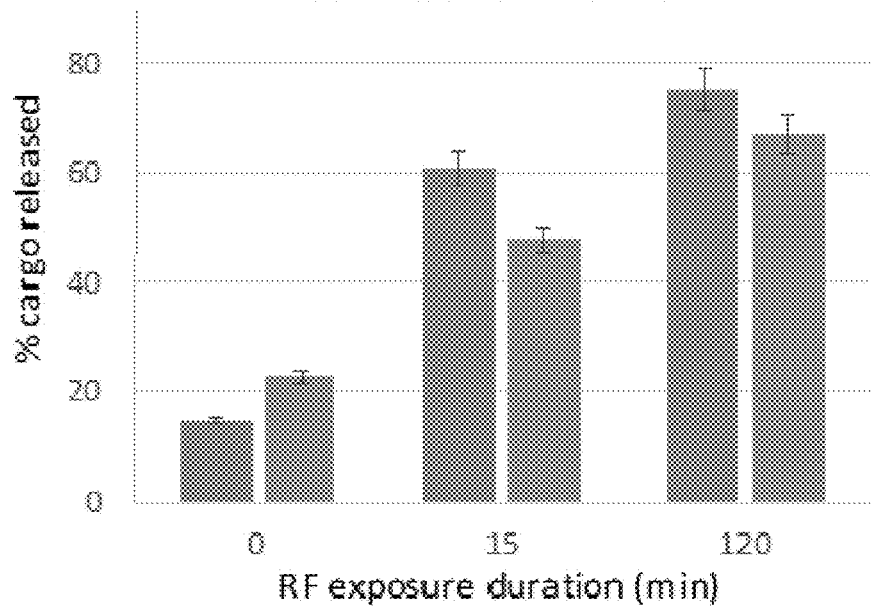
Fig. 9

SEQUENCE LISTING

```
<160> NUMBER OF SEQ ID NOS: 3

<210> SEQ ID NO 1
<211> LENGTH: 12
<212> TYPE: PRT
<213> ORGANISM: Artificial Sequence
<220> FEATURE:
<223> OTHER INFORMATION: Synthetic Construc

<400> SEQUENCE: 1

Tyr His Trp Tyr Gly Tyr Thr Pro Gln Asn Val Ile
1               5                   10

<210> SEQ ID NO 2
<211> LENGTH: 4
<212> TYPE: PRT
<213> ORGANISM: Artificial Sequence
<220> FEATURE:
<223> OTHER INFORMATION: Synthetic Construct

<400> SEQUENCE: 2

Cys Arg Gly Asp
1

<210> SEQ ID NO 3
<211> LENGTH: 5
<212> TYPE: PRT
<213> ORGANISM: Artificial Sequence
<220> FEATURE:
<223> OTHER INFORMATION: Synthetic Construct

<400> SEQUENCE: 3

Cys Arg Glu Lys Ala
1               5
```

MULTI-COMPONENT NANOCONSTRUCTS

RELATED APPLICATION

This application claims priority from U.S. Provisional Application No. 62/471,765, filed Mar. 15, 2017, the subject matter of which is incorporated herein by reference in its entirety.

GOVERNMENT FUNDING

This invention was made with government support under Grant No. CA177716 awarded by The National Institutes of Health. The United States government has certain rights in the invention.

TECHNICAL FIELD

This application relates to multi-component nanoconstructs and to the use of multi-components nanoconstructs for diagnostic and therapeutic applications.

BACKGROUND

Nanoparticles can be used as delivery vehicles for therapeutic and imaging agents to provide improved biodistribution and increased delivery efficiency of the agents to cell or tissue (e.g., solid tumors) in a subject. Advantageously, nanoparticles with more than one function can be designed that target, image, and destroy tumors. These multifunctional nanoparticles can be formed from, for example, liposomes, dendrimers, other lipidic and polymeric nanoparticles, and metal nanoparticles (e.g., iron oxide and gold). While the shape of the majority of these particles is spherical due to the methods of preparation, oblate- and rod-shaped nanostructures suitable for biomedical applications, such as gold nanorods, nanoworms, and nanonecklaces, have recently been fabricated. For example, nanoworms consist of iron oxide cores aligned along strands of high-molecular weight dextran. A nanonecklace was formed by attaching monofunctionalized gold nanoparticles onto polylysine.

SUMMARY

Embodiments described herein relate to multi-component nanoconstructs (e.g., nanochains) for use in diagnostic and therapeutic applications. The nanoconstructs can include short linear nanochains of three to five linked nanoparticles. The linked nanoparticles can be formed from at least two first nanoparticles having first functional chemical groups uniformly dispersed on the surfaces of the first nanoparticles and at least one second nanoparticle having differing second functional chemical groups uniformly dispersed on the surface of the second nanoparticle(s). The second functional chemical groups of the second nanoparticle can react with the first functional chemical groups of the at least two of first nanoparticles to link the at least two of first nanoparticles and the second nanoparticle and form the short linear nanochain that includes three to five nanoparticles.

In some embodiments, the short linear nanochain can include two first nanoparticles linked with the second nanoparticle or three first nanoparticles linked with two second particles.

In some embodiments, the nanoparticles can have an average or nominal diameter of about 1 nm to about 100 nm and the nanochain can have a length less than about 200 nm and a width about 100 nm or less.

In other embodiments, the nanoparticles forming the nanochain can be the same or different and be selected from the group consisting of a metal nanoparticle, lipidic nanoparticle, polymer nanoparticle, liposome, or dendrimer.

In some embodiments, the first nanoparticles and the second nanoparticles can have the same core material but include different functional chemical groups dispersed on the surfaces of the respective nanoparticles.

In other embodiments, at least one nanoparticle of the nanochain can include or be linked to an imaging agent, therapeutic agent, and/or targeting moiety. The therapeutic agent can include, for example, an anti-cancer agent or anti-proliferative agent. The nanochain can also include multiple targeting moieties. The targeting moieties can be linked to surfaces of the nanoparticles and the spacing between the nanoparticles can be controlled to facilitate targeting of the nanoparticles to cells of a subject. The spacing and location of the targeting moieties on each nanoparticle can be controlled to facilitate delivery, targeting, and/or therapeutic efficacy of the nanochain when administered to a subject.

In some embodiments the nanochain can include at least three metal nanoparticles. At least one of the metal nanoparticles of the nanochain can be linked to a liposome, lipidic nanoparticle, or polymer nanoparticle that includes an imaging agent or therapeutic agent. The metal nanoparticles of the nanochain when administered to a subject can be responsive to energy, from a remote source that is effective to release the imaging agent or therapeutic agent from the liposome, lipidic nanoparticle, or polymer nanoparticle. In one example, the energy can be radiofrequency (RF) energy that causes mechanical oscillation or resonance of the metal nanoparticles that is effective to release the therapeutic agent or imaging agent from the liposome, lipidic nanoparticle, or polymer nanoparticle. The RF energy effective to release the therapeutic agent or imaging agent can be an amount less than that required to induce a substantial or significant localized temperature increase in the subject.

Other embodiments described herein relate to a method of forming a multi-component nanoconstruct. The method includes suspending in a solution a plurality of first nanoparticles having first functional chemical groups uniformly dispersed on the surfaces of the first nanoparticles and a plurality of second nanoparticle having differing second functional chemical groups uniformly dispersed on the surface of the second nanoparticles. The second functional chemical groups of the second nanoparticle can react with the first functional chemical groups of at least two of the first nanoparticles upon activation to link at least two of the first nanoparticles and the second nanoparticle and form short linear nanochains that includes three to five nanoparticles.

Still other embodiments described herein relate to a system for delivering a therapeutic agent to cells or tissue of a subject using a nanoconstruct that includes a nanochain, which includes or is linked to a therapeutic agent. For example, the nanoconstruct of the system can include at least three metal nanoparticles and a liposome, lipidic nanoparticle, or polymer nanoparticle linked to at least one metal nanoparticle of the nanochain. The liposome, lipidic nanoparticle, or polymer nanoparticle can include, contain, and/ or encapsulate the therapeutic agent. The metal nanoparticles can be responsive to energy, from a remote source that is effective to release the therapeutic agent from the liposome, lipidic nanoparticle, or polymer nanoparticle after administering the nanochain to a subject. The system can further include a remote energy source for supplying energy to the metal nanoparticles effective to release the therapeutic agent from the liposome, lipidic nanoparticle, or polymer nanoparticle. The remote energy source can be external the subject being treated.

In one example, the remote energy source can include a radiofrequency (RF) energy source that produces RF energy effective cause resonating or oscillating of the nanoparticles. The RF energy effective to release the therapeutic agent can be an amount less than that required to induce a substantial or significant localized temperature increase in the subject.

BRIEF DESCRIPTION OF THE DRAWINGS

FIGS. 3A-D illustrate the characterization of the nanochain particles. (A) The size of the parent iron oxide nanoparticles and nanochains was measured using dynamic light scattering (DLS). (B) TEM images of nanochain particles are shown. The number of parent IONP being free or incorporated in nanochain was obtained from visual analysis of TEM images (minimum count was 400 particles; data presented as mean±standard deviation). (C) The size of the nanochains was measured for many weeks using DLS. The suspension was kept in PBS at room temperature. (D) The transverse (R2) relaxation rate of the nanochains was measured at 1.4 Tesla using a relaxometer.

FIGS. 4A-E illustrate histological analysis of the degree and topology of fibronectin expression in two glioma models in mice. (A) Fluorescence imaging of the entire left hemisphere of the brain shows the primary tumor and its invasive sites (5× magnification; green: CNS-1 glioma cells (GFP); blue: nuclear stain (DAPI)). (B) The abundance of fibronectin (red) is shown in the primary CNS-1 tumor (20× magnification). (C) High magnification imaging (20×) of an invasive site shows the location of fibronectin (red) with respect to the location of endothelial cells (yellow: CD31) and brain tumor cells in the same histologic section. (D) Fluorescence imaging of an entire histologic section of the brain shows the primary tumor and its invasive sites (5× magnification; green: T4121 glioma cells (GFP)). (E) High magnification imaging (20×) shows the overexpression of fibronectin (red) in the T4121 GBM.

FIGS. 5A-B illustrate evaluation of the ability of the fibronectin-targeting nanochains to deposit in brain tumors. (A) Quantification of the time course of accumulation of CREKA-targeted nanochains in the brain of mice bearing orthotopic glioma CNS-1 tumors. The animals were euthanized at 0, 1 and 8 hours after injection (n=5 mice per time point). Brains were collected and the concentration of the nanochains in tissues was quantified by direct measurement of iron using ICP-OES. Tumorbearing mice injected with saline were used for correction of the background levels of iron in the tumor tissue. (B) The deposition of CREKAtargeted nanochains was compared to their non-targeted variant and CREKA-targeted nanospheres based on the parent IONP (n=5 mice per condition). All formulations were administered at a dose containing an equal number of particles.

FIGS. 8(A-C) are illustrate TEM images of different linear nano-structures synthesized by varying the ratio between NP—COOH:NP—$NH_2$ and reaction times.

FIG. 9 illustrates a graph showing in vitro evaluation of the RF-triggered release of drugs from MPNC particles.

DETAILED DESCRIPTION

Figure 1:
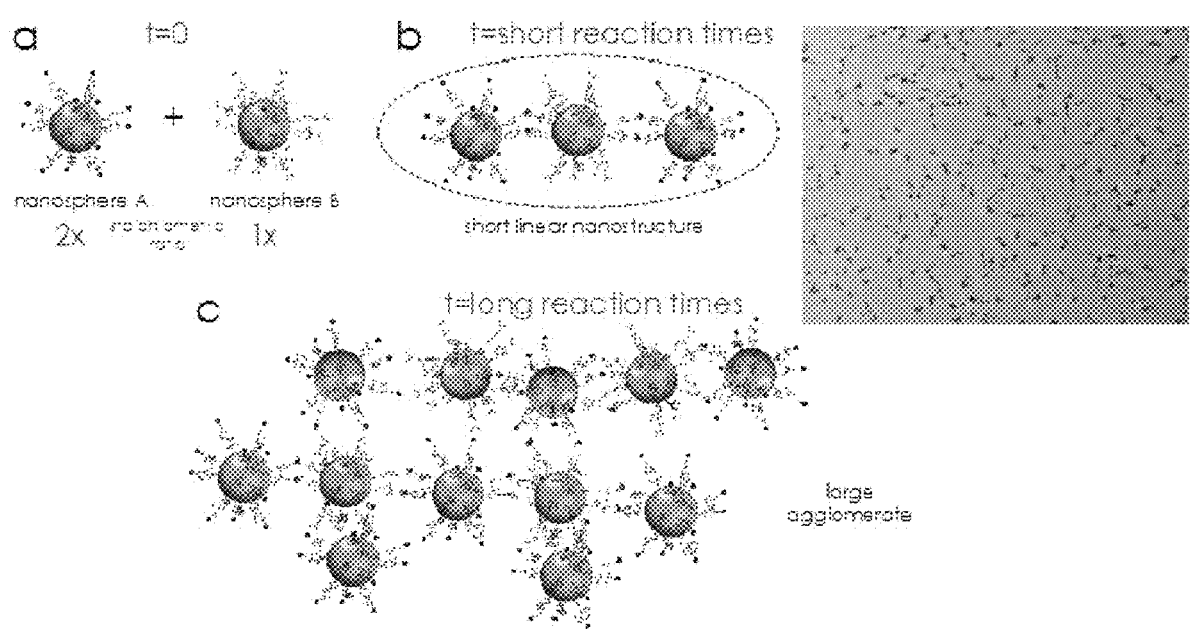
FIGS. 1A-C are a schematic illustration of the synthetic process of short linear nanostructures in accordance with an embodiment.

All scientific and technical terms used in this application have meanings commonly used in the art unless otherwise specified. The definitions provided herein are to facilitate understanding of certain terms used frequently herein and are not meant to limit the scope of the application.

The articles "a" and "an" are used herein to refer to one or to more than one (i.e., to at least one) of the grammatical object of the article. By way of example, "an element" means one element or more than one element.

As used herein, the term "sample" can refer to a specimen or culture obtained from any source, as well as clinical, research, biological and environmental samples. Biological samples may be obtained from animals (including humans) and encompass cells, fluids, solids, tissues, and organs, and whole organisms.

As used herein, the term "subject" can refer to any animal including, but not limited to, humans and non-human animals (e.g., rodents, arthropods, insects, fish (e.g., zebrafish)), non-human primates, ovines, bovines, ruminants, lagomorphs, porcines, caprines, equines, or canines felines, ayes, etc.).

As used herein, the terms "cancer" or "tumor" refer to any neoplastic growth in a subject, including an initial tumor and any metastases. The cancer can be of the liquid or solid tumor type. Liquid tumors include tumors of hematological origin, including, e.g., myelomas (e.g., multiple myeloma), leukemias (e.g., Waldenstrom's syndrome, chronic lymphocytic leukemia, other leukemias), and lymphomas (e.g., B-cell lymphomas, non-Hodgkin's lymphoma). Solid tumors can originate in organs and include cancers of the lungs, brain, breasts, prostate, ovaries, colon, kidneys and liver.

As used herein, the terms "cancer cell" or "tumor cell" can refer to cells that divide at an abnormal (i.e., increased) rate. Cancer cells include, but are not limited to, carcinomas, such as squamous cell carcinoma, non-small cell carcinoma (e.g., non-small cell lung carcinoma), small cell carcinoma (e.g., small cell lung carcinoma), basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; hematologic cancers, such as myelomas, leukemias (e.g., acute myelogenous leukemia, chronic lymphocytic leukemia, granulocytic leukemia, monocytic leukemia, lymphocytic leukemia), lymphomas (e.g., follicular lymphoma, mantle cell lymphoma, diffuse large B-cell lymphoma, malignant lymphoma, plasmocytoma, reticulum cell sarcoma, or Hodgkin's disease), and tumors of the nervous system including glioma, glioblastoma multiform, meningoma, medulloblastoma, schwannoma and epidymoma.

As used herein, the term "polynucleotide" can refer to oligonucleotides, nucleotides, or to a fragment of any of these, to DNA or RNA (e.g., mRNA, rRNA, tRNA) of genomic or synthetic origin, which may be single-stranded or double-stranded and may represent a sense or antisense strand, to peptide nucleic acids, or to any DNA-like or RNA-like material, natural or synthetic in origin, including, e.g., iRNA, ribonucleoproteins (e.g., iRNPs). The term can also encompass nucleic acids, i.e., oligonucleotides, containing known analogues of natural nucleotides. The term can also encompass nucleic acid-like structures with synthetic backbones.

As used herein, the term "polypeptide" can refer to an oligopeptide, peptide, polypeptide, or protein sequence, or to a fragment, portion, or subunit of any of these, and to naturally occurring or synthetic molecules. The term "polypeptide" can also include amino acids joined to each other by peptide bonds or modified peptide bonds, i.e., peptide isosteres, and may contain any type of modified amino acids. The term can also include peptides and polypeptide fragments, motifs and the like, glycosylated polypeptides, and all "mimetic" and "peptidomimetic" polypeptide forms.

As used herein, the term "small molecule" can refer to lipids, carbohydrates, polynucleotides, polypeptides, or any other organic or inorganic molecules.

As used herein, the term "imaging agent" can refer to a biological or chemical moiety that may be used to detect, image, and/or monitor the presence and/or progression of a cell cycle, cell function/physiology, condition, pathological disorder and/or disease.

As used herein, the terms "treating" or "treatment" of a disease can refer to executing a treatment protocol to eradicate at least one diseased cell. Thus, "treating" or "treatment" does not require complete eradication of diseased cells.

As used herein, the term "targeting moiety" can refer to a molecule or molecules that are able to bind to and complex with a biomarker. The term can also refer to a functional group that serves to target or direct a therapeutic agent or anti-cancer agent to a particular location, cell type, diseased tissue, or association. In general, a "targeting moiety" can be directed against a biomarker.

As used herein, the term "molecular signature" can refer to a unique expression pattern of one or more biomarkers (e.g., gene(s) or protein(s)) of a cell.

As used herein, the term "antibody" refers to an immunoglobulin, derivatives thereof which maintain specific binding ability, and proteins having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class, including any of the human classes: IgG, IgM, IgA, IgD, and IgE. In exemplary embodiments, antibodies used with the methods and compositions described herein are derivatives of the IgG class.

As used herein, the term "antibody fragment" refers to any derivative of an antibody which is less than full-length. In exemplary embodiments, the antibody fragment retains at least a significant portion of the full-length antibody's specific binding ability. Examples of antibody fragments include, but are not limited to, Fab, Fab', $F(ab')_2$, scFv, Fv, dsFv diabody, and Fd fragments. The antibody fragment may be produced by any means. For instance, the antibody fragment may be enzymatically or chemically produced by fragmentation of an intact antibody, it may be recombinantly produced from a gene encoding the partial antibody sequence, or it may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 10 amino acids and more typically will comprise at least about 200 amino acids.

As used herein, the term "diabodies" refers to dimeric scFvs. The components of diabodies typically have shorter peptide linkers than most scFvs and they show a preference for associating as dimers.

As used herein, the term "epitope" refers to a physical structure on a molecule that interacts with a selective component. In exemplary embodiments, epitope refers to a desired region on a target molecule that specifically interacts with a selectivity component.

As used herein, the term "Fab" refers to an antibody fragment that is essentially equivalent to that obtained by reduction of the disulfide bridge or bridges joining the two heavy chain pieces in the F(ab')$_2$ fragment. Such fragments may be enzymatically or chemically produced by fragmentation of an intact antibody, recombinantly produced from a gene encoding the partial antibody sequence, or it may be wholly or partially synthetically produced.

As used herein, the term "F(ab')$_2$" refers to an antibody fragment that is essentially equivalent to a fragment obtained by digestion of an immunoglobulin (typically IgG) with the enzyme pepsin at pH 4.0-4.5. Such fragments may be enzymatically or chemically produced by fragmentation of an intact antibody, recombinantly produced from a gene encoding the partial antibody sequence, or it may be wholly or partially synthetically produced.

As used herein, the term "Fv" refers to an antibody fragment that consists of one $V_H$ and one $V_L$ domain held together by noncovalent interactions. The term "dsFv" is used herein to refer to an Fv with an engineered intermolecular disulfide bond to stabilize the $V_H$-$V_L$ pair.

As used herein, the term "immunogen" traditionally refers to compounds that are used to elicit an immune response in an animal, and is used as such herein. However, many techniques used to produce a desired selectivity component, such as the phage display and aptamer methods described below, do not rely wholly, or even in part, on animal immunizations. Nevertheless, these methods use compounds containing an "epitope," as defined above, to select for and clonally expand a population of selectivity components specific to the "epitope." These in vitro methods mimic the selection and clonal expansion of immune cells in vivo, and, therefore, the compounds containing the "epitope" that is used to clonally expand a desired population of phage, aptamers and the like in vitro are embraced within the definition of "immunogens."

As used herein, the terms "single-chain Fvs" and "scFvs" refers to recombinant antibody fragments consisting of only the variable light chain ($V_L$) and variable heavy chain ($V_H$) covalently connected to one another by a polypeptide linker. Either $V_L$ or $V_H$ may be the NH$_2$-terminal domain. The polypeptide linker may be of variable length and composition so long as the two variable domains are bridged without serious steric interference. In exemplary embodiments, the linkers are comprised primarily of stretches of glycine and serine residues with some glutamic acid or lysine residues interspersed for solubility.

An "effective amount" can refer to that amount of a therapeutic agent that results in amelioration of symptoms or a prolongation of survival in the subject and relieves, to some extent, one or more symptoms of the disease or returns to normal (either partially or completely) one or more physiological or biochemical parameters associated with or causative of the disease. Therapeutic agents can include any agent (e.g., molecule, drug, pharmaceutical composition, etc.) capable of preventing, inhibiting, or arresting the symptoms and/or progression of a disease.

Embodiments described herein relate to multi-component nano-scale nanoconstructs (e.g., nanochain) that can be used for diagnostic and therapeutic applications. The nanoconstructs can include short linear nanochains of three to five linked nanoparticles. The nanochain can be linear or substantially linear and have an oblate nano-scale or high-aspect ratio shape with a length less than about 500 nm (e.g., about 100 nm to about 300 nm) and a width less than about two times the length of the nanochain (e.g., less than about three times or less than about four times the length of the nanochain). For example, the width of the nanochain can be about 50 nm or less, for example, about 10 nm to about 40 nm for a nanochain with a length of about 100 nm to about 150 nm. The oblate shape of the nanochain allows the nanochain when administered to a subject to have prolonged circulation in the subject compared to administration of nanoparticles alone. Advantageously, contrary to nanoparticle spheres that move along the center of a vessel in microcirculation, the oblate-shaped nanochains described herein can drift laterally in circulation moving in close proximity to the endothelium. This allows the nanochain to interact with vessel walls to, for example, target vascular specific biomarkers or extravasate through leaky tumor endothelium in tumor interstitium.

The nanochains described herein can be used in diagnostic, therapeutic, and/or theranostic applications to deliver therapeutic agents and/or imaging agents to cells and/or tissue of a subject as well as actively target cells and/or tissue of a subject upon systemic administration (e.g., intravenous, intravascular, intraarterial infusion) of the nanochains to the subject. The nanochains can also be remotely activated with a remote energy source to selectively release therapeutic agents and/or imaging agents bound or coupled to the nanochains to targeted cells and/or tissue of the subject.

The linked nanoparticles can include at least two first nanoparticles having first functional chemical groups uniformly dispersed on the surfaces of the first nanoparticles and at least one second nanoparticle having differing second functional chemical groups uniformly dispersed on the surface of the second nanoparticle(s). The second functional chemical groups of the second nanoparticle can react with the first functional chemical groups of the at least two of first nanoparticles to link the at least two of first nanoparticles and the second nanoparticle and form the short linear nanochain that includes three to five nanoparticles.

FIG. 1b illustrates an example of a linear multi-component nanochain of a nanoconstruct in accordance with an embodiment described herein. The linear nanochain has an oblate shape and a length of about 100 nm to about 300 nm and a width of about 10 nm to about 100 nm. The nanochain includes three nanoparticles that are linked together to form the nanochain. Although a linear nanochain with three nano-particles is illustrated, the nanochain can include, for example, four, or five nanoparticles linked together.

The nanoparticles used to form the nanochains can include any material that can be formed into a nanoparticle (or nanoshell or nanomembrane) with nano-scale dimensions (e.g., about 1 nm to about 100 nm) and to which can be provide an asymmetric surface chemistry. Examples of nanoparticles can include metal nanoparticles, lipidic nanoparticles, polymer nanoparticles, liposomes, dendrimer, quantum dots, and/or combinations of these materials. In some embodiments, the nanoparticles can be optically or magnetically detectable. In other embodiments, intrinsically fluorescent or luminescent nanoparticles, nanoparticles that comprise fluorescent or luminescent moieties, plasmon resonant nanoparticles, and magnetic nanoparticles are among the detectable nanoparticles that can be used.

In general, the nanoparticles can have dimensions small enough to allow the nanochain to be systemically administered to a subject and targeted to cells and tissue of the subject. In some embodiments, the nanoparticles can have a size that facilitates extravasation of the nanochain in cancer therapy or diagnosis. Typically, the nanoparticles can have a longest straight dimension (e.g., diameter) of about 100 nm or less. In some embodiments, the nanoparticles have a diameter of 50 nm or less. Smaller nanoparticles, e.g., having diameters of 30 nm or less, e.g., about 1 nm to about 30 nm or about 1 nm to about 5 nm, are used in some embodiments.

The nanoparticles of the nanochain may be uniform (e.g., being about the same size) or of variable size. Particles may be any shape (e.g., spherical or rod shaped), but are preferably made of regularly shaped material (e.g., spherical). In some embodiments, the geometry or structure of the nanoparticles can incorporate the functional capabilities of nanotip, nanosphere, and nanoring geometries. Other geometries can include spherical, circular, triangle, quasi-triangle, square, rectangular, hexagonal, oval, elliptical, rectangular with semi-circles or triangles and the like. Selection of suitable materials and geometries are known in the art.

In some embodiments, the nanoparticles can include quantum dots, i.e., bright, fluorescent nanocrystals with physical dimensions small enough such that the effect of quantum confinement gives rise to unique optical and electronic properties. In certain embodiments, the nanoparticles are optically detectable nanoparticles, such as metal nanoparticles. Metals used to form the nanoparticles include, but not limited to, Ag, Au, Cu, Al, Fe, Co, Ni, Ru, Rh, Pd, and Pt or oxides thereof. In another embodiment, the metal comprises Fe or iron oxide (e.g., FeO, $Fe_2O_3$, and $Fe_3O_4$). A further surface functional layer can be added or formed in combination with a metal core material. Such functional layers can include, but are not limited to, Ag oxide, Au oxide, $SiO_2$, $Al_2O_3$, $Si_3N_4$, $Ta_2O_5$, $TiO_2$, ZnO, $ZrO_2$, $HfO_2$, $Y_2O_3$, tin oxide, antimony oxide, iron oxide, and other oxides; Ag doped with chlorine or chloride, Au doped chlorine or chloride, Ethylene and Chlorotrifluoroethylene (ECTFE), Poly(ethylene-co-butyl acrylate-co-carbon monoxide) (PEBA), Poly(allylamine hydrochloride) (PAH), Polystyrene sulfonate (PSS), Polytetrafluoroethylene (PTFE), Polyvinyl alcohol (PVA), Polyvinyl chloride (PVC), Polyvinyldene fluoride (PVDF), Polyvinylproroli-done (PVP), and other polymers; stacked multiple layers at least two layers including above listed metal layers and non-metal layers, and the like. In some embodiments, the metal core can be Au, Ag, Fe, Ti, Ni, Cr, Pt, Ru, NiCr alloy, NiCrN, PtRh alloy, CuAuCo alloy, IrRh alloy and/or WRe alloy. The metals used should be biocompatible.

In some embodiments, the nanoparticle can be a magnetic nanoparticle. "Magnetic particles" refers to magnetically responsive particles that contain one or more metals or oxides or hydroxides thereof. Nanochains including optically detectable metal nano-particles or quantum dots can be detected in vivo upon systemic administration to a subject using magnetic resonance imaging (MRI), magnetic resonance spectroscopy (MRS), nuclear magnetic resonance imaging (NMR), multimodal imaging, fluorescent, positron emission tomography (PET), near infrared (NIR) imaging, X-ray imaging, and computed tomography (CT).

In other embodiments, the nanoparticles can include lipidic nanoparticles, polymer nanoparticles, liposomes, and/or dendrimers with a membrane, shell, or surface that is formed from a naturally-occurring, synthetic or semi-synthetic (i.e., modified natural) material. In some embodiments, the lipidic nanoparticles or liposomes can include a membrane or shell that is formed from a naturally-occurring, synthetic or semi-synthetic material that is generally amphipathic (i.e., including a hydrophilic component and a hydrophobic component). Examples of materials that can be used to form the membrane or shell of the lipidic nanoparticle or liposome include lipids, such as fatty acids, neutral fats, phospholipids, oils, glycolipids, surfactants, aliphatic alcohols, waxes, terpenes and steroids. Semi-synthetic or modified natural lipids can include natural lipids that have been chemically modified in some fashion. The lipid can be neutrally-charged, negatively-charged (i.e., anionic), or positively-charged (i.e., cationic). Examples of anionic lipids can include phosphatidic acid, phosphatidyl glycerol, and fatty acid esters thereof, amides of phosphatidyl ethanolamine, such as anandamides and methanandamides, phosphatidyl serine, phosphatidyl inositol and fatty acid esters thereof, cardiolipin, phosphatidyl ethylene glycol, acidic lysolipids, sulfolipids and sulfatides, free fatty acids, both saturated and unsaturated, and negatively-charged derivatives thereof. Examples of cationic lipids can include N-[1-(2,3-dioleoyloxy)propyl]-N,N,N-trimethyl-ammonium chloride and common natural lipids derivatized to contain one or more basic functional groups.

Other examples of lipids, any one or combination of which may be used to form the membrane or shell of the lipidic nano-particle or liposome, can include: phosphocholines, such as 1-alkyl-2-acetoyl-sn-glycero 3-phosphocholines, and 1-alkyl-2-hydroxy-sn-glycero 3-phosphocholines; phosphatidylcholine with both saturated and unsaturated lipids, including dioleoylphosphatidylcholine, dimyristoylphosphatidylcholine, dipentadecanoylphosphatidylcholine, dilauroylphosphatidylcholine, dipalmitoylphosphatidylcholine (DPPC), distearoylphosphatidylcholine (DSPC), and diarachidonylphosphatidylcholine (DAPC); phosphatidylethanolamines, such as dioleoylphosphatidylethanolamine, dipalmitoylphosphatidylethanolamine (DPPE), and distearoylphosphatidylethanolamine (DSPE); phosphatidylserine; phosphatidylglycerols, including distearoylphosphatidylglycerol (DSPG); phosphatidylinositol; sphingolipids, such as sphingomyelin; glycolipids, such as ganglioside GM1 and GM2; glucolipids; sulfatides; glycosphingolipids; phosphatidic acids, such as dipalmitoylphosphatidic acid (DPPA) and distearoylphosphatidic acid (DSPA); palmitic acid; stearic acid; arachidonic acid; oleic acid; lipids bearing polymers, such as chitin, hyaluronic acid, polyvinylpyrrolidone or polyethylene glycol (PEG); lipids bearing sulfonated mono-, di-, oligo- or polysaccharides; cholesterol, cholesterol sulfate, and cholesterol hemisuccinate; tocopherol hemisuccinate; lipids with ether and ester-linked fatty acids; polymerized lipids (a wide variety of which are well known in the art); diacetyl phosphate; dicetyl phosphate; stearylaamine; cardiolipin; phospholipids with short chain fatty acids of about 6 to about 8 carbons in length; synthetic phospholipids with asymmetric acyl chains, such as, for example, one acyl chain of about 6 carbons and another acyl chain of about 12 carbons; ceramides; non-ionic liposomes including niosomes, such as polyoxyalkylene (e.g., polyoxyethylene) fatty acid esters, polyoxyalkylene (e.g., polyoxyethylene) fatty alcohols, polyoxyalkylene (e.g., polyoxyethylene) fatty alcohol ethers, polyoxyalkylene (e.g., polyoxyethylene) sorbitan fatty acid esters (such as, for example, the class of compounds referred to as TWEEN (commercially available from ICI Americas, Inc., Wilmington, Del.), glycerol polyethylene glycol oxystearate, glycerol polyethylene glycol ricinoleate, alkyloxylated (e.g., ethoxylated) soybean sterols, alkyloxylated (e.g., ethoxylated) castor oil, polyoxyethylene-polyoxypropylene polymers, and polyoxyalkylene (e.g., polyoxyethylene) fatty acid stearates; sterol aliphatic acid esters including cholesterol sulfate, cholesterol butyrate, cholesterol isobutyrate, cholesterol palmitate, cholesterol stearate, lanosterol acetate, ergosterol palmitate, and phytosterol n-butyrate; sterol esters of sugar acids including cholesterol glucuronide, lanosterol glucuronide, 7-dehydrocholesterol glucuronide, ergosterol glucuronide, cholesterol gluconate, lanosterol gluconate, and ergosterol gluconate; esters of sugar acids and alcohols including lauryl glucuronide, stearoyl glucuronide, myristoyl glucuronide, lauryl gluconate, myristoyl gluconate, and stearoyl gluconate; esters of sugars and aliphatic acids including sucrose laurate, fructose laurate, sucrose palmitate, sucrose stearate, glucuronic acid, gluconic acid and polyuronic acid; saponins including sarsasapogenin, smilagenin, hederagenin, oleanolic acid, and digitoxigenin; glycerol dilaurate, glycerol trilaurate, glycerol dipalmitate, glycerol and glycerol esters including glycerol tripalmitate, glycerol distearate, glycerol tristearate, glycerol dimyristate, glycerol trimyristate; long chain alcohols including n-decyl alcohol, lauryl alcohol, myristyl alcohol, cetyl alcohol, and n-octadecyl alcohol; 6-(5-cholesten-3β-yloxy)-1-thio-β-D-galactopyranoside; digalactosyldiglyceride; 6-(5-cholesten-3β-yloxy)hexyl-6-amino-6-deoxy-1-thio-β-D-galactopyranoside; 6-(5-cholesten-3β-yloxy)hexyl-6-amino-6-deoxyl-1-thio-α-D-mannopyranoside; 12-(((7'-diethylaminocoumarin-3-yl)carbonyl)methylamino)octadecanoic acid; N-[12-(((7'-diethylaminocoumarin-3-yl)carbonyl)methylamino)octadecanoyl]-2-aminopalmitic acid; cholesteryl(4'-trimethylammonio)butanoate; N-succinyldioleoylphosphatidylethanolamine; 1,2-dioleoyl-sn-glycerol; 1,2-dipalmitoyl-sn-3-succinylglycerol; 1,3-dipalmitoyl-2-succinylglycerol; 1-hexadecyl-2-palmitoylglycerophosphoethanolamine and palmitoylhomocysteine; and/or any combinations thereof.

The first functional chemical groups and second functional chemical groups uniformly dispersed on the respective surfaces of the first nanoparticles and second nanoparticles can define first linkers and second linkers between the first nanoparticles and second nanoparticles.

The first linkers and second linkers can be of any suitable length and contain any suitable number of atoms and/or subunits to provide an oblate and/or liner nanochain. The linkers can include one or combination of chemical and/or biological moieties. Examples of chemical moieties can include alkyl groups, methylene carbon chains, ether, polyether, alkyl amide linkers, alkenyl chains, alkynyl chains, disulfide groups, and polymers, such as poly(ethylene glycol) (PEG), functionalized PEG, PEG-chelant polymers, dendritic polymers, and combinations thereof. Examples of biological moieties can include peptides, modified peptides, streptavidin-biotin or avidin-biotin, polyaminoacids (e.g., polylysine), polysaccharides, glycosaminoglycans, oligonucleotides, phospholipid derivatives, and combinations thereof.

In some embodiments, the first linker can include a first polymer tether and a first end group. The second linker can include a second polymer tether and second end group. The first end groups and the second groups of the first linkers and second linkers disposed on separate nanoparticles can bind or complex to link the separate nanoparticles.

The first polymer tethers of the first linkers and the second polymer tether of the second linkers can be formed of any flexible polymer chain that can be bound to and extend from the nanoparticles and provided with a first end group or second group. In some embodiment, the first polymer tether 50 and the second polymer tether 54 can include biocompatible polymer, such as polyethylene glycol (PEG) (MW about 500 to 50,000 and 1000 to 10,000); polypropylene glycol (MW about 500 to about 50,000), dextran, and derivatives such as amino-dextran and carboxy-dextran, and polysaccharides. The first polymer tether and the second polymer tether can be attached directly or indirectly to the nanoparticles and/or a coating layer disposed on the nanoparticle.

Agents used to coat the nanoparticles include anti-agglomerations modifiers, such as citric acid, as well as amphiphilic polymers, detergents and/or a lipid structures including detergent derivatives and lipid derivatives. The amphiphilic polymers can include, but are not limited to hydrocarbons and DTPA modified poly(acrylic acid), poly (maleic acid), poly(maleic anhydride), and the like. The detergents can include, but are not limited to, AOT, brij family, Igepal family, triton family, SDS, or derivatives of each. In particular, the detergents can include, dioctyl sulfosuccinate sodium salt, polyethylene glycol dodecyl ether, (octylphenoxy) polyethoxyethanol, octylphenyl-polyethylene glycol, t-octylphenoxypolyethoxyethanol, polyethylene glycol tert-octylphenyl ether, 4-(1,1,3,3-tetramethylbutyl) phenyl-polyethylene glycol, dodecyl sulfate sodium salt, or glycolic acid ethoxylate octyl ether. Further, the block copolymer can include lipids such as, but not limited to, lipid-PEG, natural lipids, synthetic lipids, sphingolipids, or derivatives of each.

In particular, the block copolymer can include an ABC triblock structure having a poly-butylacrylate segment, a poly-ethylacrylate segment, or a poly-methacrylic acid segment, for example. The block copolymer can include a diblock and/or triblock copolymer having two or more different poly-aliphatic-acrylate segments. In addition, the block copolymer can include a diblock and/or triblock copolymer having two or more poly-alkyl-acrylate segments.

In some embodiement, the nanoparticles can include citric acid coated iron oxide nanoparticles. The citric acid coated iron oxide nanoparticles can be prepared by reacting iron oxide nanoparticles in an aqueiouls solution with a citric acid solution.

The first polymer tether and the second polymer tether can be linked to the nanoparticle directly or indirectly by any means. For example, the first polymer tether and the second polymer tether can be linked to the nanoparticle using a covalent link, a non-covalent link, an ionic link, and a chelated link, as well as being absorbed or adsorbed onto the nanoparticles. In addition, the first polymer tether and the second polymer tether can be linked to the nanoparticles through hydrophobic interactions, hydrophilic interactions, charge-charge interactions, π-stacking interactions, combinations thereof, and like interactions.

The first end groups and the second end groups of the first polymer linkers and the second polymer linkers can include functional groups that are reactive with, complex with, or bind to each other to allow the first linkers and second linkers of separate nanoparticles to bind and link the separate nanoparticles using solid phase synthesis techniques. The functional groups can include, for example, amines, carboxylic acids, hydroxyls, thiols, and combinations thereof that can potentially react with each other to link separate nanoparticle. In one embodiment, the first end group can comprise an amine group and the second end group can comprise a carboxyl group that is reactive with the amine group.

The nanochains can be prepared by suspending in a solution (e.g., non-aqueous solution) a plurality of the first nanoparticles having first functional chemical groups uniformly dispersed on the surfaces of the first nanoparticles and a plurality of the second nanoparticles having differing second functional chemical groups uniformly dispersed on the surface of the second nanoparticles. The second functional chemical groups of the second nanoparticle can react with the first functional chemical groups of the at least two of first nanoparticles upon activation and agitation of the solution to link the at least two of first nanoparticles and the second nanoparticle and form short linear nanochains that includes three to five nanoparticles.

By way of example, particle A is decorated with amine groups (NP—NH$_2$), whereas particle B is decorated with carboxyl groups (NP—COOH). Upon activation of the carboxyl groups on the NP—COOH particles, particles A and B will react with each other forming larger agglomerates. By performing the reaction in an organic solvent (i.e., absence of water), hydrolysis of the activated COOH intermediate is constrained. Thus, the reaction rate and growth of the agglomerate are dictated by mixing (e.g., stirring rate) and concentration of the starting particles. Assuming that NP—NH$_2$ and NP—COOH particles are mixed at a ratio of about 2:1. At early time points, two NP—NH$_2$ particles will react with one 'activated' NP—COOH forming a short linear nanochain. If the reaction is allowed to continue, the particles will continue growing into large agglomerates. The reaction time and conditions can optimized so that well-defined linear, short nanochains of, for example, three to five nanoparticles are formed. This one-pot synthetic approach can be applied to different classes of nanoparticles (e.g., iron oxide, gold, silica, etc.) and sizes.

In some embodiments, the nanochains can additionally or optionally include at least one targeting moiety that is capable of targeting and/or adhering the nanochain to a cell or tissue of interest. The targeting moiety can comprise any molecule, or complex of molecules, which is/are capable of interacting with an intracellular, cell surface, or extracellular biomarker of the cell. The biomarker can include, for example, a cellular protease, a kinase, a protein, a cell surface receptor, a lipid, and/or fatty acid. Other examples of biomarkers that the targeting moiety can interact with include molecules associated with a particular disease. For example, the biomarkers can include cell surface receptors implicated in cancer development, such as epidermal growth factor receptor and transferrin receptor, or cancer metastasis, such as $\alpha_v\beta_3$ integrin. The targeting moieties can interact with the biomarkers through, for example, non-covalent binding, covalent binding, hydrogen binding, van der Waals forces, ionic bonds, hydrophobic interactions, electrostatic interaction, and/or combinations thereof.

The targeting moieties can include, but are not limited to, synthetic compounds, natural compounds or products, macromolecular entities, bioengineered molecules (e.g., polypeptides, lipids, polynucleotides, antibodies, antibody fragments), and small entities (e.g., small molecules, neurotransmitters, substrates, ligands, hormones and elemental compounds).

In one example, the targeting moiety can include an antibody, such as a monoclonal antibody, a polyclonal antibody, or a humanized antibody. The antibody can include Fv fragments, single chain Fv (scFv) fragments, Fab' fragments, F(ab')2 fragments, single domain antibodies, camelized antibodies and other antibody fragments. The antibody can also include multivalent versions of the foregoing antibodies or fragments thereof including monospecific or bispecific antibodies, such as disulfide stabilized Fv fragments, scFv tandems ((scFv)$_2$ fragments), diabodies, tribodies or tetrabodies, which typically are covalently linked or otherwise stabilized (i.e., leucine zipper or helix stabilized) scFv fragments; and receptor molecules, which naturally interact with a desired target molecule.

Preparation of antibodies can be accomplished by any number of methods for generating antibodies. These methods typically include the step of immunization of animals, such as mice or rabbits, with a desired immunogen (e.g., a desired target molecule or fragment thereof). Once the mammals have been immunized, and boosted one or more times with the desired immunogen(s), antibody-producing hybridomas may be prepared and screened according to well known methods. See, for example, Kuby, Janis, Immunology, Third Edition, pp. 131-139, W.H. Freeman & Co. (1997), for a general overview of monoclonal antibody production, that portion of which is incorporated herein by reference.

In vitro methods that combine antibody recognition and phage display techniques can also be used to allow one to amplify and select antibodies with very specific binding capabilities. See, for example, Holt, L. J. et al., "The Use of Recombinant Antibodies in Proteomics," Current Opinion in Biotechnology, 2000, 11:445-449, incorporated herein by reference. These methods typically are much less cumbersome than preparation of hybridomas by traditional monoclonal antibody preparation methods.

In some embodiments, phage display technology may be used to generate a targeting moiety specific for a desired target molecule. An immune response to a selected immunogen is elicited in an animal (such as a mouse, rabbit, goat or other animal) and the response is boosted to expand the immunogen-specific B-cell population. Messenger RNA is isolated from those B-cells, or optionally a monoclonal or polyclonal hybridoma population. The mRNA is reverse-transcribed by known methods using either a poly-A primer or murine immunoglobulin-specific primer(s), typically specific to sequences adjacent to the desired $V_H$ and $V_L$ chains, to yield cDNA. The desired $V_H$ and $V_L$ chains are amplified by polymerase chain reaction (PCR) typically using $V_H$ and $V_L$ specific primer sets, and are ligated together, separated by a linker. $V_H$ and $V_L$ specific primer sets are commercially available, for instance from Stratagene, Inc. of La Jolla, Calif. Assembled $V_H$-linker-$V_L$ product (encoding a scFv fragment) is selected for and amplified by PCR. Restriction sites are introduced into the ends of the $V_H$-linker-$V_L$ product by PCR with primers including restriction sites and the scFv fragment is inserted into a suitable expression vector (typically a plasmid) for phage display. Other fragments, such as a Fab' fragment, may be cloned into phage display vectors for surface expression on phage particles. The phage may be any phage, such as lambda, but typically is a filamentous phage, such as Fd and M13, typically M13.

In phage display vectors, the $V_H$-linker-$V_L$ sequence is cloned into a phage surface protein (for M13, the surface proteins g3p (pIII) or g8p, most typically g3p). Phage display systems also include phagemid systems, which are based on a phagemid plasmid vector containing the phage surface protein genes (for example, g3p and g8p of M13) and the phage origin of replication. To produce phage particles, cells containing the phagemid are rescued with helper phage providing the remaining proteins needed for the generation of phage. Only the phagemid vector is packaged in the resulting phage particles because replication of the phagemid is grossly favored over replication of the helper phage DNA. Phagemid packaging systems for production of antibodies are commercially available. One example of a commercially available phagemid packaging system that also permits production of soluble ScFv fragments in bacterial cells is the Recombinant Phage Antibody System (RPAS), commercially available from Amersham Pharmacia Biotech, Inc. of Piscataway, N.J. and the pSKAN Phagemid Display System, commercially available from MoBiTec, LLC of Marco Island, Fla. Phage display systems, their construction, and screening methods are described in detail in, among others, U.S. Pat. Nos. 5,702,892, 5,750,373, 5,821,047 and 6,127,132, each of which is incorporated herein by reference in their entirety.

The targeting moiety need not originate from a biological source. The targeting moiety may, for example, be screened from a combinatorial library of synthetic peptides. One such method is described in U.S. Pat. No. 5,948,635, incorporated herein by reference, which described the production of phagemid libraries having random amino acid insertions in the pIII gene of M13. These phage may be clonally amplified by affinity selection as described above.

The immunogens used to prepare targeting moieties having a desired specificity will generally be the target molecule, or a fragment or derivative thereof. Such immunogens may be isolated from a source where they are naturally occurring or may be synthesized using methods known in the art. For example, peptide chains may be synthesized by 1-ethyl-3-[dimethylaminoproply]carbodiimide (EDC)-catalyzed condensation of amine and carboxyl groups. In certain embodiments, the immunogen may be linked to a carrier bead or protein. For example, the carrier may be a functionalized bead such as SASRIN resin commercially available from Bachem, King of Prussia, Pa. or a protein such as keyhole limpet hemocyanin (KLH) or bovine serum albumin (BSA). The immunogen may be attached directly to the carrier or may be associated with the carrier via a linker, such as a non-immunogenic synthetic linker (for example, a polyethylene glycol (PEG) residue, amino caproic acid or derivatives thereof) or a random, or semi-random polypeptide.

In certain embodiments, it may be desirable to mutate the binding region of the polypeptide targeting moiety and select for a targeting moiety with superior binding characteristics as compared to the un-mutated targeting moiety. This may be accomplished by any standard mutagenesis technique, such as by PCR with Taq polymerase under conditions that cause errors. In such a case, the PCR primers could be used to amplify scFv-encoding sequences of phagemid plasmids under conditions that would cause mutations. The PCR product may then be cloned into a phagemid vector and screened for the desired specificity, as described above.

In other embodiments, the targeting moieties may be modified to make them more resistant to cleavage by proteases. For example, the stability of targeting moiety comprising a polypeptide may be increased by substituting one or more of the naturally occurring amino acids in the (L) configuration with D-amino acids. In various embodiments, at least 1%, 5%, 10%, 20%, 50%, 80%, 90% or 100% of the amino acid residues of targeting moiety may be of the D configuration. The switch from L to D amino acids neutralizes the digestion capabilities of many of the ubiquitous peptidases found in the digestive tract. Alternatively, enhanced stability of a targeting moiety comprising a peptide bond may be achieved by the introduction of modifications of the traditional peptide linkages. For example, the introduction of a cyclic ring within the polypeptide backbone may confer enhanced stability in order to circumvent the effect of many proteolytic enzymes known to digest polypeptides in the stomach or other digestive organs and in serum. In still other embodiments, enhanced stability of a targeting moiety may be achieved by intercalating one or more dextrorotatory amino acids (such as, dextrorotatory phenylalanine or dextrorotatory tryptophan) between the amino acids of targeting moiety. In exemplary embodiments, such modifications increase the protease resistance of a targeting moiety without affecting the activity or specificity of the interaction with a desired target molecule.

In certain embodiments, a targeting moiety as described herein may comprise a homing peptide, which selectively directs the nanoparticle to a targeted cell. Homing peptides for a targeted cell can be identified using various methods well known in the art. Many laboratories have identified the homing peptides that are selective for cells of the vasculature of brain, kidney, lung, skin, pancreas, intestine, uterus, adrenal gland, retina, muscle, prostate, or tumors. See, for example, Samoylova et al., 1999, Muscle Nerve, 22:460; Pasqualini et al., 1996 Nature, 380:364; Koivunen et al., 1995, Biotechnology, 13:265; Pasqualini et al., 1995, J. Cell Biol., 130:1189; Pasqualini et al., 1996, Mole. Psych., 1:421, 423; Rajotte et al., 1998, J. Clin. Invest., 102:430; Rajotte et al., 1999, J. Biol. Chem., 274:11593. See, also, U.S. Pat. Nos. 5,622,6999; 6,068,829; 6,174,687; 6,180,084; 6,232, 287; 6,296,832; 6,303,573; and 6,306,365.

Phage display technology provides a means for expressing a diverse population of random or selectively randomized peptides. Various methods of phage display and methods for producing diverse populations of peptides are well known in the art. For example, methods for preparing diverse populations of binding domains on the surface of a phage have been described in U.S. Pat. No. 5,223,409. In particular, phage vectors useful for producing a phage display library as well as methods for selecting potential binding domains and producing randomly or selectively mutated binding domains are also provided in U.S. Pat. No. 5,223,409. Similarly, methods of producing phage peptide display libraries, including vectors and methods of diversifying the population of peptides that are expressed, are also described in Smith et al., 1993, Meth. Enzymol., 217:228-257, Scott et al., Science, 249:386-390, and two PCT publications WO 91/07141 and WO 91/07149. Phage display technology can be particularly powerful when used, for example, with a codon based mutagenesis method, which can be used to produce random peptides or randomly or desirably biased peptides (see, e.g., U.S. Pat. No. 5,264, 563). These or other well-known methods can be used to produce a phage display library, which can be subjected to the in vivo phage display method in order to identify a peptide that homes to one or a few selected tissues.

In vitro screening of phage libraries has previously been used to identify peptides that bind to antibodies or cell surface receptors (see, e.g., Smith, et al., 1993, Meth. Enzymol., 217:228-257). For example, in vitro screening of phage peptide display libraries has been used to identify novel peptides that specifically bind to integrin adhesion receptors (see, e.g., Koivunen et al., 1994, J. Cell Biol. 124:373-380), and to the human urokinase receptor (Goodson, et al., 1994, Proc. Natl. Acad. Sci., USA 91:7129-7133).

In certain embodiments, the targeting moiety may comprise a receptor molecule, including, for example, receptors, which naturally recognize a specific desired molecule of a target cell. Such receptor molecules include receptors that have been modified to increase their specificity of interaction with a target molecule, receptors that have been modified to interact with a desired target molecule not naturally recognized by the receptor, and fragments of such receptors (see, e.g., Skerra, 2000, J. Molecular Recognition, 13:167-187). A preferred receptor is a chmokine receptor. Exemplary chemokine receptors have been described in, for example, Lapidot et al, 2002, Exp Hematol, 30:973-81 and Onuffer et al, 2002, Trends Pharmacol Sci, 23:459-67.

In some embodiments, the targeting moiety can be targeting peptide comprising an EGF peptide. The EGF peptide may comprise the amino acid sequence YHWYGYTPQNVI-amide (SEQ ID NO: 1). The peptide may be synthesized by any method known in the art. For example, the EGF peptide may be synthesized manually using Fmoc protected amino acids (Peptides International, Louisville, Ky.) on rink-amide CLEAR resin (Peptides International, Louisville, Ky., 100-200 mesh size, 0.4 milliequivalents/gram).

In other embodiments, the targeting moiety can include cyclic tripeptide arginine-glycine-aspartic acid (cRGD) (SEQ ID NO: 2), which is ligand for vascular targeting and metastasis.

In other embodiments, the targeting peptide can include a CREKA (SEQ ID NO: 3) targeting peptide that specifically binds to fibronectin-related complexes in metastatic tumors.

In still other embodiments, the targeting moiety may comprise a ligand molecule, including, for example, ligands which naturally recognize a specific desired receptor of a target cell, such as a Transferrin (Tf) ligand. Such ligand molecules include ligands that have been modified to increase their specificity of interaction with a target receptor, ligands that have been modified to interact with a desired receptor not naturally recognized by the ligand, and fragments of such ligands.

In other embodiments, the targeting moiety may comprise an aptamer. Aptamers are oligonucleotides that are selected to bind specifically to a desired molecular structure of the target cell. Aptamers typically are the products of an affinity selection process similar to the affinity selection of phage display (also known as in vitro molecular evolution). The process involves performing several tandem iterations of affinity separation, e.g., using a solid support to which the diseased immunogen is bound, followed by polymerase chain reaction (PCR) to amplify nucleic acids that bound to the immunogens. Each round of affinity separation thus enriches the nucleic acid population for molecules that successfully bind the desired immunogen. In this manner, a random pool of nucleic acids may be "educated" to yield aptamers that specifically bind target molecules. Aptamers typically are RNA, but may be DNA or analogs or derivatives thereof, such as, without limitation, peptide nucleic acids (PNAs) and phosphorothioate nucleic acids.

In yet other embodiments, the targeting moiety may be a peptidomimetic. By employing, for example, scanning mutagenesis to map the amino acid residues of a protein, which is involved in binding other proteins, peptidomimetic compounds can be generated which mimic those residues which facilitate the interaction. Such mimetics may then be used as a targeting moiety to deliver the composition to a target cell. For instance, non-hydrolyzable peptide analogs of such resides can be generated using benzodiazepine (e.g., see Freidinger et al. in Peptides: Chemisty and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopeptides (Ewenson et al., 1986, J Med Chem 29:295; and Ewenson et al., in Peptides: Structure and Function (Proceedings of the 9th American Peptide Symposium) Pierce Chemical Co. Rockland, Ill., 1985), b-turn dipeptide cores (Nagai et al., 1985, Tetrahedron Lett 26:647; and Sato et al., 1986, J Chem Soc Perkin Trans 1:1231), and (3-aminoalcohols (Gordon et al., 1985, Biochem Biophys Res Cummun 126:419; and Dann et al., 1986, Biochem Biophys Res Commun 134:71).

The targeting moiety can be coupled to nanoparticles of the nanochain using a linker. The linker can be of any suitable length and contain any suitable number of atoms and/or subunits. The linker can include one or combination of chemical and/or biological moieties. Examples of chemical moieties can include alkyl groups, methylene carbon chains, ether, polyether, alkyl amide linkers, alkenyl chains, alkynyl chains, disulfide groups, and polymers, such as poly(ethylene glycol) (PEG), functionalized PEG, PEG-chelant polymers, dendritic polymers, and combinations thereof. Examples of biological moieties can include peptides, modified peptides, streptavidin-biotin or avidin-biotin, polyaminoacids (e.g., polylysine), polysaccharides, glycosaminoglycans, oligonucleotides, phospholipid derivatives, and combinations thereof.

In some embodiments, the nanoconstructs can include multiple types of targeting moieties and the spacing and location of the targeting moieties on each nanoparticle can be controlled to facilitate delivery, targeting, and/or therapeutic efficacy of the nanochain. In other embodiments, the targeting moieties on the surface of the nanoparticles and the spacing between the nanoparticles can be controlled to facilitate targeting of the nanoparticles to cells of a subject.

In other embodiments, the nanoconstructs can include imaging agents (or detectable moieties) and/or therapeutic agents that are encapsulated by (e.g., within liposome, lipidic nanoparticle, or polymer nanoparticle), contained in (e.g., polymer nanoparticles or dendrimers), or conjugated to the nanoparticles. Therapeutic agents encapsulated by, contained in, and/or linked to the nanoparticles can include any substance capable of exerting a biological or therapeutic effect in vitro and/or in vivo. Therapeutic agents can also include any therapeutic or prophylactic agent used in the treatment (including the prevention, diagnosis, alleviation, or cure) of a malady, affliction, condition, disease or injury in a subject. Examples of therapeutic agents include, but are not limited to anti-cancer agents, anti-proliferative agents, and chemotherapeutic agents. The therapeutic agents can be in the form of biologically active ligands, small molecules, peptides, polypeptides, proteins, DNA fragments, DNA plasmids, interfering RNA molecules, such as siRNAs, oligonucleotides, and DNA encoding for shRNA.

Imaging agents can include any substance that may be used for imaging or detecting a region of interest (ROI) in a subject and/or diagnosing the presence or absence of a disease or diseased tissue in a subject. The imaging agent can be selected such that it generates a signal, which can be measured and whose intensity is related (preferably proportional) to the distribution of the imaging agent and nanochain in the subject. Examples of imaging agents include, but are not limited to: radionuclides, fluorescent dyes, chemiluminescent agents, colorimetric labels, and magnetic labels. In one example, the imaging agent can include a radiolabel that is detected using gamma imaging wherein emitted gamma irradiation of the appropriate wavelength is detected. Methods of gamma imaging include, but are not limited to, SPECT and PET. For SPECT detection, the chosen radiolabel can lack a particular emission, but will produce a large number of photons in, for example, a 140-200 keV range. For PET detection, the radiolabel can be a positron-emitting moiety, such as 19F.

In another example, the imaging can an include MRS/MRI radiolabel, such as gadolinium, $^{19}F$, $^{13}C$, that is coupled (e.g., attached or complexed) with the nanochain using general organic chemistry techniques. The imaging agent can also include radiolabels, such as $^{18}F$, $^{11}C$, $^{75}Br$, or $^{76}Br$ for PET by techniques well known in the art and are described by Fowler, J. and Wolf, A. in POSITRON EMISSION TOMOGRAPHY AND AUTORADIOGRAPHY (Phelps, M., Mazziota, J., and Schelbert, H. eds.) 391-450 (Raven Press, N Y 1986) the contents of which are hereby incorporated by reference. The imaging can also include 1231 for SPECT.

The imaging agent can further include known metal radiolabels, such as Technetium-99m (99mTc). Preparing radiolabeled derivatives of Tc99m is well known in the art. See, for example, Zhuang et al., "Neutral and stereospecific Tc-99m complexes: [99mTc]N-benzyl-3,4-di-(N-2-mercaptoethyl)-amino-pyrrolidines (P-BAT)" Nuclear Medicine & Biology 26(2):217-24, (1999); Oya et al., "Small and neutral Tc(v)O BAT, bisaminoethanethiol (N2S2) complexes for developing new brain imaging agents" Nuclear Medicine & Biology 25(2):135-40, (1998); and Hom et al., "Technetium-99m-labeled receptor-specific small-molecule radiopharmaceuticals: recent developments and encouraging results" Nuclear Medicine & Biology 24(6):485-98, (1997).

In some embodiments, the therapeutic agent can be an anti-cancer agent or anti-proliferative agent that is encapsulated by, contained in, and/or linked to the nanoparticles. The phrase "anti-cancer agent" or "anti-proliferative agent" can include agents that exert antineoplastic, chemotherapeutic, antiviral, antimitotic, antitumorgenic, and/or immunotherapeutic effects, e.g., prevent the development, maturation, or spread of neoplastic cells, directly on the tumor cell, e.g., by cytostatic or cytocidal effects, and not indirectly through mechanisms. There are a large number of anti-proliferative agent agents available in commercial use, in clinical evaluation and in pre-clinical development, which can be administered in combination with the nanochain.

The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category.

Examples of antimetabolite antineoplastic agents include, but are not limited to acanthifolic acid, aminothiadiazole, anastrozole, bicalutamide, brequinar sodium, capecitabine, carmofur, Ciba-Geigy CGP-30694, cladribine, cyclopentyl cytosine, cytarabine phosphate stearate, cytarabine conjugates, cytarabine ocfosfate, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, finasteride, floxuridine, fludarabine phosphate, N-(2'-furanidyl)-5-fluorouracil, Daiichi Seiyaku F0-152, fluorouracil (5-FU), 5-FU-fibrinogen, isopropyl pyrrolizine, Lilly LY-188011, Lilly LY-264618, methobenzaprim, methotrexate, Wellcome MZPES, nafarelin, norspermidine, nolvadex, NCI NSC-127716, NCI NSC-264880, NCI NSC-39661, NCI NSC-612567, Warner-Lambert PALA, pentostatin, piritrexim, plicamycin, Asahi Chemical PL-AC, stearate; Takeda TAC-788, thioguanine, tiazofurin, Erbamont TIF, trimetrexate, tyrosine kinase inhibitors, tyrosine protein kinase inhibitors, Taiho UFT, toremifene, and uricytin, all of which are disclosed in U.S. Pat. No. 6,916,800, which is herein incorporated by reference in its entirety.

Examples of alkylating-type anti-proliferative agents include, but are not limited to, Shionogi 254-S, aldo-phosphamide analogues, altretamine, anaxirone, Boehringer Mannheim BBR-2207, bestrabucil, budotitane, Wakunaga CA-102, carboplatin, carmustine (BiCNU), Chinoin-139, Chinoin-153, chlorambucil, cisplatin, cyclophosphamide, American Cyanamid CL-286558, Sanofi CY-233, cyplatate, dacarbazine, Degussa D-19-384, Sumimoto DACHP(Myr) 2, diphenylspiromustine, diplatinum cytostatic, Erba distamycin derivatives, Chugai DWA-2114R, ITI E09, elmustine, Erbamont FCE-24517, estramustine phosphate sodium, etoposide phosphate, fotemustine, Unimed G-6-M, Chinoin GYKI-17230, hepsul-fam, ifosfamide, iproplatin, lomustine, mafosfamide, mitolactol, mycophenolate, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, thiotepa, Yakult Honsha SN-22, spiromustine, Tanabe Seiyaku TA-077, tauromustine, temozolomide, teroxirone, tetraplatin and trimelamol.

Examples of antibiotic-type anti-proliferative agents that may be used in the present invention include, but are not limited to Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

Examples of hormonal-type anti-proliferative agents that may be used in the present invention include, but are not limited to Abarelix; Abbott A-84861; Abiraterone acetate; Aminoglutethimide; anastrozole; Asta Medica AN-207; Antide; Chugai AG-041R; Avorelin; aseranox; Sensus B2036-PEG; Bicalutamide; buserelin; BTG CB-7598; BTG CB-7630; Casodex; cetrolix; clastroban; clodronate disodium; Cosudex; Rotta Research CR-1505; cytadren; crinone; deslorelin; droloxifene; dutasteride; Elimina; Laval University EM-800; Laval University EM-652; epitiostanol; epristeride; Mediolanum EP-23904; EntreMed 2-ME; exemestane; fadrozole; finasteride; flutamide; formestane; Pharmacia & Upjohn FCE-24304; ganirelix; goserelin; Shire gonadorelin agonist; Glaxo Wellcome GW-5638; Hoechst Marion Roussel Hoe-766; NCI hCG; idoxifene; isocordoin; Zeneca ICI-182780; Zeneca ICI-118630; Tulane University J015X; Schering Ag J96; ketanserin; lanreotide; Milkhaus LDI-200; letrozol; leuprolide; leuprorelin; liarozole; lisuride hydrogen maleate; loxiglumide; mepitiostane; Leuprorelin; Ligand Pharmaceuticals LG-1127; LG-1447; LG-2293; LG-2527; LG-2716; Bone Care International LR-103; Lilly LY-326315; Lilly LY-353381-HCl; Lilly LY-326391; Lilly LY-353381; Lilly LY-357489; miproxifene phosphate; Orion Pharma MPV-2213ad; Tulane University MZ-4-71; nafarelin; nilutamide; Snow Brand NKS01; octreotide; Azko Nobel ORG-31710; Azko Nobel ORG-31806; orimeten; orimetene; orimetine; ormeloxifene; osaterone; Smithkline Beecham SKB-105657; Tokyo University OSW-1; Peptech PTL-03001; Pharmacia & Upjohn PNU-156765; quinagolide; ramorelix; Raloxifene; statin; sandostatin LAR; Shionogi S-10364; Novartis SMT-487; somavert; somatostatin; tamoxifen; tamoxifen methiodide; teverelix; toremifene; triptorelin; TT-232; vapreotide; vorozole; Yamanouchi YM-116; Yamanouchi YM-511; Yamanouchi YM-55208; Yamanouchi YM-53789; Schering AG ZK-1911703; Schering AG ZK-230211; and Zeneca ZD-182780.

Miscellaneous antineoplastic agents include, but not limited to alpha-carotene, alpha-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-10, bromofosfamide, Wellcome BW-502, Wellcome BW-773, calcium carbonate, Calcet, Calci-Chew, Calci-Mix, Roxane calcium carbonate tablets, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Cell Pathways CP-461, Yakult Honsha CPT-11, crisnatol, curaderm, cytochalasin B, cytarabine, cytocytin, Merz D-609, DABIS maleate, dacarbazine, datelliptinium, DFMO, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel, Encore Pharmaceuticals E7869, elliprabin, elliptinium acetate, Tsumura EPMTC, ergotamine, etoposide, etretinate, EULEXIN, Cell Pathways EXISU-LIND (sulindac sulphone or CP-246), fenretinide, Merck Research Labs Finasteride, Florical, Fujisawa FR-57704, gallium nitrate, gemcitabine, genkwadaphnin, Gerimed, Chugai GLA-43, Glaxo GR-63178, grifolan NMF-5N, hexadecylphosphocholine, Green Cross HO-221, homoharringtonine, hydroxyurea, BTG ICRF-187, ilmofosine, irinotecan, isoglutamine, isotretinoin, Otsuka JI-36, Ramot K-477, ketoconazole, Otsuak K-76COONa, Kureha Chemical K-AM, MECT Corp KI-8110, American Cyanamid L-623, leucovorin, levamisole, leukoregulin, lonidamine, Lundbeck LU-23-112, Lilly LY-186641, Materna, NCI (US) MAP, marycin, Merrel Dow MDL-27048, Medco MEDR-340, megestrol, merbarone, merocyanine derivatives, methylanilinoacridine, Molecular Genetics MGI-136, minactivin, mitonafide, mitoquidone, Monocal, mopidamol, motretinide, Zenyaku Kogyo MST-16, Mylanta, N-(retinoyl)amino acids, Nilandron; Nisshin Flour Milling N-021, N-acylateddehydroalanines, nafazatrom, Taisho NCU-190, Nephro-Calci tablets, nocodazole derivative, Normosang, NCI NSC-145813, NCI NSC-361456, NCI NSC-604782, NCI NSC-95580, octreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, retinoids, Encore Pharmaceuticals R-flurbiprofen, Sandostatin; Sapporo Breweries RBS, restrictin-P, retelliptine, retinoic acid, Rhone-Poulenc RP-49532, Rhone-Poulenc RP-56976, Scherring-Plough SC-57050, Scherring-Plough SC-57068, seienium (selenite and selenomethionine), SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, Sugen SU-101, Sugen SU-5416, Sugen SU-6668, sulindac, sulindac sulfone; superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides, Yamanouchi YM-534, Zileuton, ursodeoxycholic acid, and Zanosar.

In some embodiments, the therapeutic agents can be loaded into and/or onto the nanoparticles and/or nanoconstructs by encapsulation, absorption, adsorption, and/or non-covalent linkage of the therapeutic agent to or within a nanoparticle of the nanochain. The amount of therapeutic agent loaded onto or in the nanoparticle can be controlled by changing the size of the nanoparticle or the composition of the nanoparticle.

In some embodiments, release of the therapeutic agent from the nanoparticle of the nanochain can occur by desorption, diffusion through the polymer or lipid coating, or polymer or lipid wall, nanoparticle erosion, and/or disruption of the nanoparticle structure, which can all be controlled by the type of the nanoparticle, i.e., having it become swollen or degradable in the chosen microenvironment.

In other embodiments, release of the therapeutic agent or imaging agent from the nanoconstruct can be remotely triggered by a remote energy source that supplies energy to the nanochain effective to release the therapeutic agent or imaging agent from the nanoparticle. In one embodiment, the multi-component nanoconstruct can include a nanochain, which comprises at least three metal nanoparticles, and a liposome, lipidic nanoparticle, or polymer nanoparticle linked to the nanochain to form the nanoconstruct. The liposome, lipidic nanoparticle, or polymer nanoparticle can encapsulate or contain the therapeutic agent (e.g., chemotherapeutic agent, such as doxorubicin). The metal nanoparticles of the nanochain can be responsive to energy, from a remote source that is effective to release the therapeutic agent from the liposome, lipidic nanoparticle, or polymer nanoparticle after administering the nanochain to a subject. The remote source can be external or remote from a subject, which allows non-invasive remote release of the therapeutic agent to the subject. Advantageously, a nanoconstruct that allows remote release of the therapeutic agent, such as a chemotherapeutic agent (e.g., doxorubicin) can target or be targeted to specific cells or tissue of subject, such as tumors, cancers, and metastases, by systemic administration (e.g., intravenous, intravascular, or intraarterial infusion) to the subject and once targeted to the cells or tissue remotely released to specifically treat the targeted cells or tissue of subject (e.g., tumors, cancers, and metastasis). Targeting and selective release of the chemotherapeutic agents to malignant cancer metastases allows treatment of such metastases using chemotherapeutics, which would provide an otherwise neglible effect if not targeted and remotely released using the nanochains described herein.

In some embodiments, mild radiofrequency (RF) energy from a remote RF energy source can generate a magnetic field that can be used to release a therapeutic agent or imaging agent from liposome, lipidic nanoparticle, or polymer nanoparticles that are linked to a linear nanochain of metal nanoparticles. The liposome, lipidic nanoparticle, or polymer nanoparticle can have a membrane or shell that encapsulates or contains a therapeutic agent or imaging agent. The liposome, lipidic nanoparticle, or polymer nanoparticle can readily release the therapeutic agent or imaging agent upon mechanical disruption of the membrane or shell. The linked metal particles of the nanochain can be responsive to RF energy from a remote RF energy source and act as a mechanic transducer to mechanically resonate or oscillate upon application of RF energy from the energy source. Application of mild RF energy from RF source can rapidly release the therapeutic agent or imaging agent from the liposome, lipidic nanoparticle, or polymer nanoparticle membrane or shell due to defects in the membrane or shell cause by oscillation of the metal nanoparticle tail. The mild RF energy applied to the nanochain can be that amount effective cause the metal nano-particles to mechanically resonate or oscillate at an amount or level effective to disrupt liposome, lipidic nanoparticle, or polymer nanoparticle membrane or shell and release the therapeutic agent from the liposome, lipidic nanoparticle, or polymer nanoparticle without causing significant heating (e.g., greater than 1° C., 2° C., 3° C., or 5° C.) around the nanochain when administered to a subject.

Figure 7:
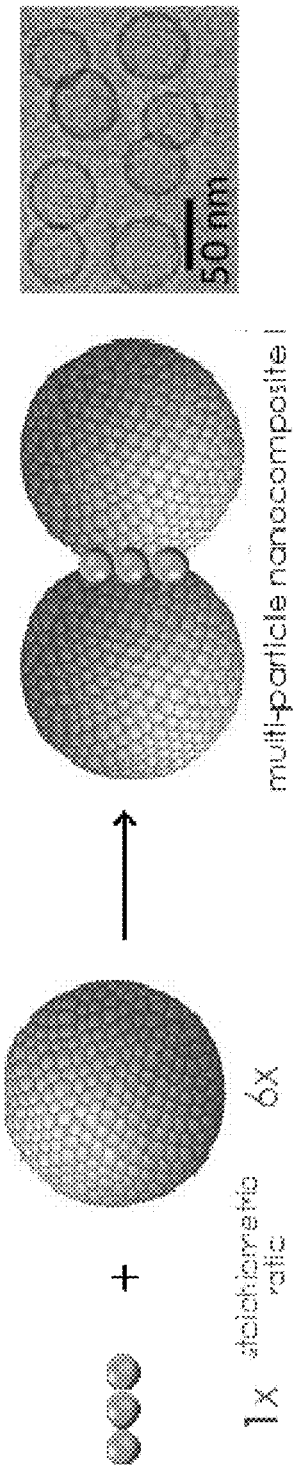
FIG. 7 is a schematic illustratrion of higher-order multiparticle nanocomposite particles.

By way of example, a multi-component nanoconstruct that includes a linear nanochain of three iron oxide nanoparticles that is linked two liposomes containing a therapeutic agent (e.g., chemotherapeutic agent) is shown in FIG. 7. The iron oxide nanoparticles can have a nominal or average diameter of about 10 nm to about 30 nm (e.g., about 20 nm) and the liposomes can have a nominal diameter of about 30 nm to about 200 nm (e.g., about 100 nm). The nanochain can be linear or substantially linear and have oblate nano-scale shape with a length of about 100 nm to about 150 nm and a width of about 10 nm to about 50 nm.

The nanoconstruct can also include one or multiple types of targeting moieties (not shown) that are linked to the nanoparticles and/or liposome and allow the nanoconstruct to be targeted to, for example, a tumor, cancer cell, or metastasis. Examples of targeting moieties include an integrand targeting peptide, CREKA targeting peptide, and EGFR targeting peptide.

Upon administration of the nanoconstruct to a subject by, for example, intravascular administration, the nanoconstruct can target the tumor, cancer, or metastases being treated. The nanoconstruct can be imaged by, for example, magnetic resonance imaging or computed tomography, to confirm localization and targeting of the nanochain to the tumor or cancer cells. The nanoconstruct targeted to the tumor, cancer, or metastases can be applied mild RF energy from a remote RF energy that is external to the subject being treated to mechanically resonate or oscillate the iron oxide nanoparticlez of the nanoconstruct and rapidly release the therapeutic agent from the liposome membrane or shell due to defects in the membrane or shell cause by oscillation of the iron oxide nanoparticlez.

It will be appreciated that other remote energy sources can be used to release the therapeutic agent or imaging agent from the nanoconstruct and that the selection of the energy source will depend at least in part on the nanoparticles used to form the nanochain. For example, the nanochain can include a chain of metal nanoparticles, such as gold nanoparticles, that are linked to a thermosensitive liposome, lipidic nanoparticle, or polymer nanoparticle that contains or encapsulates a therapeutic agent or imaging agent. Electromagnetic radiation can be applied to the nanochain after administration to a subject from a remote energy source, such as a remote near infrared laser, to cause the gold nanoparticles to heat to a temperature (e.g., about 40 C to about 45 C) effective to disrupt the thermosensitive liposome, lipidic nanoparticle, or polymer nanoparticle and release the therapeutic agent from liposome, lipidic nanoparticle, or polymer nanoparticle. Gold nanoparticles can efficiently convert photons from the remote energy source to heat. The remote energy source can be, for example, a minimally invasive laser that can be inserted in vivo in the subject being treated or positioned external or ex vivo the subject. The energy from laser can be in the near infrared range to allow deep radiation penetration into tissue and remote release of therapeutic agent or imaging agent.

In some embodiments, the nanoconstruct described herein can be formulated in a pharmaceutical composition. Formulation of pharmaceutical composition for use in the modes of administration noted below (and others) are described, for example, in Remington's Pharmaceutical Sciences (18$^{th}$ edition), ed. A. Gennaro, 1990, Mack Publishing Company, Easton, Pa. (also see, e.g., M. J. Rathbone, ed., Oral Mucosal Drug Delivery, Drugs and the Pharmaceutical Sciences Series, Marcel Dekker, Inc., N.Y., U.S.A., 1996; M. J. Rathbone et al., eds., Modified-Release Drug Delivery Technology, Drugs and the Pharmaceutical Sciences Series, Marcel Dekker, Inc., N.Y., U.S.A., 2003; Ghosh et al., eds., Drug Delivery to the Oral Cavity, Drugs and the Pharmaceutical Sciences Series, Marcel Dekker, Inc., N.Y. U.S.A., 1999.

For example, pharmaceutical compositions can contain can be in the form of a sterile aqueous solution containing, if desired, additional ingredients, for example, preservatives, buffers, tonicity agents, antioxidants, stabilizers, nonionic wetting or clarifying agents, and viscosity increasing agents.

Examples of preservatives for use in such a solution include benzalkonium chloride, benzethonium chloride, chlorobutanol, thimerosal and the like. Examples of buffers include boric acid, sodium and potassium bicarbonate, sodium and potassium borates, sodium and potassium carbonate, sodium acetate, and sodium biphosphate, in amounts sufficient to maintain the pH at between about pH 6 and about pH 8, and for example, between about pH 7 and about pH 7.5. Examples of tonicity agents are dextran 40, dextran 70, dextrose, glycerin, potassium chloride, propylene glycol, and sodium chloride.

Examples of antioxidants and stabilizers include sodium bisulfite, sodium metabisulfite, sodium thiosulfite, and thiourea. Examples of wetting and clarifying agents include polysorbate 80, polysorbate 20, poloxamer 282 and tyloxapol. Examples of viscosity-increasing agents include gelatin, glycerin, hydroxyethylcellulose, hydroxmethylpropylcellulose, lanolin, methylcellulose, petrolatum, polyethylene glycol, polyvinyl alcohol, polyvinylpyrrolidone, and carboxymethylcellulose Examples of formulations for parenteral administration can include aqueous solutions of the composition in water-soluble form, for example, water-soluble salts and alkaline solutions. Especially preferred salts are maleate, fumarate, succinate, S,S tartrate, or R,R tartrate. In addition, suspensions of the composition as appropriate oily injection suspensions can be administered. Aqueous injection suspensions can contain substances that increase the viscosity of the suspension, such as sodium carboxymethyl cellulose, sorbitol and/or dextran. Optionally, the suspension may also contain stabilizers.

Formulations for topical administration to the skin include, for example, ointments, creams, gels and pastes comprising the composition in a pharmaceutical acceptable carrier. The formulation of the composition for topical use includes the preparation of oleaginous or water-soluble ointment bases, as is well known to those in the art. For example, these formulations may include vegetable oils, animal fats, and, for example, semisolid hydrocarbons obtained from petroleum. Particular components used may include white ointment, yellow ointment, cetyl esters wax, oleic acid, olive oil, paraffin, petrolatum, white petrolatum, spermaceti, starch glycerite, white wax, yellow wax, lanolin, anhydrous lanolin and glyceryl monostearate. Various water-soluble ointment bases may also be used, including glycol ethers and derivatives, polyethylene glycols, polyoxyl 40 stearate and polysorbates.

In some embodiments, the nanoconstructs described herein can be used in a method for treating a disorder in a subject. The disorder can include diseased cells. The cells can include a diseased cell or healthy cell that is derived from, or a part of, various tissue types, such as neuronal tissue (including both neuron and glia), connective tissue, hepatic tissue, pancreatic tissue, kidney tissue, bone marrow tissue, cardiac tissue, retinal tissue, intestinal tissue, lung tissue, endothelium tissue, cartilage, skeletal muscle, cardiac muscle, other cardiac tissue that is not muscle, smooth muscle, bone, tendon, ligament, adipose tissue and skin. Depending upon the particular application, the cell may be in vivo or ex vivo. Ex vivo cells can be collected as part of one or more samples using one or a combination of known techniques (e.g., biopsy) and, if needed, further processed (e.g., centrifuged) prior to culture, analysis, etc.

In some embodiments, a therapeutically effective amount of the nanoconstructs can be administered in vivo to a subject to treat the subject. The nanoconstructs may be administered by any convenient route, such as by infusion or bolus injection or by absorption through epithelial or mucocutaneous linings (e.g., oral mucosa, vaginal, rectal and intestinal mucosa, etc.), and may be administered together with other biologically active agents. For example, the nanochains may be introduced into the central nervous system by any suitable route, including intraventricular injection, intrathecal injection, or intraventricular injection via an intraventricular catheter that is attached to a reservoir.

The nanoconstructs can also be delivered systematically (e.g., intravenously), regionally, or locally (e.g., intra- or peri-tumoral injection) by, for example, intraarterial, intratumoral, intravenous, parenteral, intrapneural cavity, topical, oral or local administration, as well as subcutaneous, intrazacheral (e.g., by aerosol), or transmucosal (e.g., voccal, bladder, vaginal, uterine, rectal, nasal, mucosal). If delivery of the nanochains to the brain is desired, the targeted nanoparticles can be injected into an artery of the carotid system of arteries (e.g., occipital artery, auricular artery, temporal artery, cerebral artery, maxillary artery etc.). As discussed above, the nanochains can be formulated as a pharmaceutical composition for in vivo administration.

The nanoconstructs can be administered to the subject at an amount effective to provide a desired result(s) and to avoid undesirable physiological results. The precise dose to be employed can also depend on the route of administration, and should be decided according to the judgment of a medical practitioner and each subject's circumstances. In addition, known in vitro and in vivo assays may optionally be employed to help identify optimal dosage ranges. Effective doses may be extrapolated from dose-response curves derived from in vitro or in vivo test systems.

The nanoconstructs can be administered in a variety of unit dosage forms, depending upon the particular cell or tissue being treated, the general medical condition of each subject, the method of administration, and the like. Details on dosages are well described in the scientific literature. The exact amount and concentration of the targeted nanochains, or the "effective dose", can be routinely determined (e.g., by a medical practitioner). The "dosing regimen" will depend upon a variety of factors, such as whether the cell or tissue to be treated is disseminated or local, the general state of the subject's health, the subject's age, and the like. Using guidelines describing alternative dosing regimens, e.g., from the use of other agents and compositions, the skilled artisan can readily determine by routine trials the optimal effective concentrations of the composition.

In some embodiments, the nanoconstructs described herein can be use with in vivo imaging methods where detection and imaging of cells or tissue cannot readily be performed with traditional optical detection or imaging techniques. These methods can include, for example, endovascular detection, cancer and metastasis imaging, infection or inflammation imaging, imaging of cell and tissue apoptosis, localization of neurologic pathways involved in chronic pain, and localization of epilepsy foci. It will be appreciated that the nanochains can be used in other in vivo methods as well as intraoperative procedures.

In each method, a plurality of the nanoconstructs can be delivered to the cells or tissue of the subject in vivo by administering an effective amount or concentration of the nanochains to the subject. By effective amount or concentration of the nanochains, it is meant an amount of the nanochains that are effective for detecting and imaging the target cells or tissue. As apparent to one skilled in the art, such an amount will vary depending on factors that include the amount of tissue to be imaged, the rate of contact of the nanochains with the tissue, any abnormalities of the tissue that may affect the efficiency of the nanochains contacting or binding to the tissue.

In some embodiments, the nanoconstructs can be administered to the subject by venous (or arterial) infusion. In venous infusion, an effective amount or concentration of the nanochains administered to subject can be that amount or concentration that is detectable in the tissue or cells after sequestration of the nanochains in the liver, spleen, and lymph nodes. Optionally, the nanoconstructs can be administered to the subject by directly injecting the nanochains into cells or tissue of the area being identified or an area proximate or peripheral to the area being identified. Direct injection of the nanoconstructs can be performed by using, for example, a syringe.

In other embodiments, the nanoconstructs can be administered to a subject for imaging at least one region of interest (ROI) of the subject. The ROI can include a particular area or portion of the subject and, in some instances, two or more areas or portions throughout the entire subject. The ROI can include, for example, pulmonary regions, gastrointestinal regions, cardiovascular regions (including myocardial tissue), renal regions, as well as other bodily regions, tissues, lymphocytes, receptors, organs and the like, including the vasculature and circulatory system, and as well as diseased tissue, including neoplastic or cancerous tissue. The ROI can include regions to be imaged for both diagnostic and therapeutic purposes. The ROI is typically internal; however, it will be appreciated that the ROI may additionally or alternatively be external.

At least one image of the ROI can be generated using an imaging modality once the nanochains localize to the ROI. The imaging modality can include one or combination of known imaging techniques capable of visualizing the nanochains. Examples of imaging modalities can include ultrasound (US), magnetic resonance imaging (MRI), nuclear magnetic resonance (NMR), computed topography (CT), electron spin resonance (ESR), nuclear medical imaging, optical imaging, and positron emission topography (PET).

In one example, the nanoconstruct can be detected with MRI and/or x-ray. MRI relies upon changes in magnetic dipoles to perform detailed anatomic imaging and functional studies. The electron dense core of nanoparticles of the nanoconstruct, such as metal nanoparticles, can also make them highly visible on X-ray, monochromatic X-ray, computed tomography (CT) and ultrasound (US).

Optionally, the nanoparticles of the nanochain can be modified to facilitate detection and imaging with MRI and CT as well as positron emission tomography (PET). For MRI applications, gadolinium tags can be attached to the shell and/or iron oxide can be as nanoparticles in the nanochain. For PET applications, radioactive tags can be attached to nanoparticles. For CT applications, iodide or other heavy metals can be attached to the nanoparticles to facilitate CT contrast.

It will be appreciated the nanoconstructs will likely be most useful clinically when several imaging techniques or imaging followed by a medical or surgical procedure is used. In this way, the ability to use one agent for multiple imaging modalities is optimized making the nanochains cost-competitive with existing contrast agents.

For multimodal imaging applications, the nanoconstructs can be administered to a subject and then preoperatively imaged using, for example, CT or MRI. After preoperative imaging, the nanoconstructs can serve as optical beacons for use during surgery leading to more complete resections or more accurate biopsies. In surgical resection of lesions, the completeness of resection can be assessed with intra-operative ultrasound, CT, or MRI. For example, in glioma (brain tumor) surgery, the nanoconstructs can be given intravenously about 24 hours prior to pre-surgical stereotactic localization MRI. The nanoconstructs can be imaged on gradient echo MRI sequences as a contrast agent that localizes with the glioma.

In other embodiments, the nanoconstructs can be administered to a subject to treat and/or image a neoplastic disease in subject. Neoplastic diseases treatable by the nanochains described herein can include disease states in which there are cells and/or tissues which proliferate abnormally. One example of a neoplastic disease is a tumor. The tumor can include a solid tumor, such as a solid carcinoma, sarcoma or lymphoma, and/or an aggregate of neoplastic cells. The tumor may be malignant or benign, and can include both cancerous and pre-cancerous cells. The neoplastic disease can also include cancer and malignant cancer metastases.

A composition comprising the nanoconstructs describe herein that includes an anti-cancer agent or anti-proliferative agent can be formulated for administration (e.g., injection) to a subject diagnosed with at least one neoplastic disorder. The nanoconstructs can be formulated according to method as described above and include, for example, at least one therapeutic agent or imaging agent as well as targeting moiety to target the neoplastic cells or cancer cells.

The following examples are for the purpose of illustration only and are not intended to limit the scope of the claims, which are appended hereto.

Example 1

This example describes the assembly of different types (e.g., iron oxide, gold, silica, etc.) and sizes (e.g., 5-100 nm) of nanoparticles into a higher-order nanoparticle constructs or nanochains that can be used for both diagnosis and treatment of various diseases, such as cancer and neurodegenerative diseases. The nanoparticle constructs or nanoconstructs can be formed using a synthetic one-pot approach. The parent nanoparticles can be nanospheres that form stable suspension in an organic solvent. The suspension consists of two different types of nanospheres based on the functional chemical group on the surface of the nanospheres. For example, nanosphere A can be decorated with Polyethylene Glycol (PEG) molecules with amine groups on their distal end (termed NS—$NH_2$). Nanosphere B can be decorated with PEG-COOH (termed NS—COOH). Upon activation of the carboxyl groups on the NS—COOH particles, the nanospheres A and B will react with each other forming larger agglomerates. In the absence of water (hydrolysis of the activated COOH intermediate), the reaction rate and growth of the agglomerate is dictated by mixing (e.g., stirring rate) and concentration of the nanospheres. Assuming that NS—$NH_2$ and NS—COOH nanospheres are mixed at a ratio of 2:1 (FIG. 1A). At early time points, two NS—$NH_2$ nanospheres will react with one 'activated' NS—COOH forming a linear 3-member nanostructure (FIG. 1B). If the reaction is allowed to continue, the nanostructure will continue growing into a large agglomerate (FIG. 1C). In addition to the reaction conditions, we have identified the time point where arrest of the reaction results in well-defined short nanoconstructs (i.e., FIG. 1B).

Upon exchange of the organic solvent with an aqueous buffer, a second type of nanoparticles (e.g., drug-loaded liposomes) can be added to the short linear nanostructure. Using the appropriate cross-linker and different ratios, liposomes and linear nanostructures are chemically link into higher-order multi-particle nano-constructs (MPNC) with a high degree of precision as shown in FIG. 7.

Details of Synthetic Process
Synthesis of Parent Iron Oxide Nanospheres
Synthesis and Characterization of Functionalized Iron Oxide Nanoparticles Iron oxide nanoparticles were synthesized in a three-neck flask by coprecipitation method. Briefly, 0.6757 g of $FeCl_3.6H_2O$ and 0.2478 g of $FeCl_2.4H_2O$ were dissolved in 5 mL of deoxygenated water. To this solution, 2.5 mL of 0.4 M HCl was added under vigorous stirring. This iron precursor solution was added to a solution of 25 mL of 0.5 M NaOH, which was preheated to 80° C. under a constant flow of argon. The solution became black immediately after the addition of the iron precursor solution, indicating the formation of iron oxide nanoparticles. The reaction mixture was then stirred for another 15 minutes at 80° C. under argon and the black precipitate was separated by using a powerful magnet. The nanoparticles were then washed several times with Milli-Q water until stable ferrofluid was obtained. To prevent the nanoparticles from agglomeration citric acid (170 mg of citric acid in 10 mL of water) was introduced and allowed to react at 80° C. for 1.5 hours. The pH of the reaction mixture was adjusted to 5.2 using concentrated ammonia solution prior to heating. The reaction was protected under argon in order to avoid any undesired sidereactions. Finally uncoated nanoparticles and aggregates were removed by repeated centrifugation. Excess citric acid was removed by centrifugation with Amicon® Ultra-15 centrifugal filters.

Surface Modification of Iron Oxide Nanoparticles with Silane-PEG-NH$_2$

The pH of 10 mg of citric acid coated nanoparticles at 1 mg/mL concentration was adjusted to 11 with concentrated ammonia. To this solution, 10 mg of silane-PEG-NH$_2$ was added and the reaction was allowed to proceed for 24 hours with shaking. The resulting nanoparticle solution was heated at 80° C. for 2 hours in order to achieve covalent linkage between polymer chains and the particle surface. Finally, the resulting functionalized nanoparticles (Fe$_3$O$_4$@silane-PEG-NH$_2$) were centrifuged at 4000 rpm for 10 min using Amicon® Ultra-15 centrifugal filters. The concentrated product (termed NS—NH$_2$ in FIG. 1) was stored at 4° C.

Surface Modification of Iron Oxide Nanoparticles with Silane-PEG-COOH

The pH of 10 mg of citric acid coated nanoparticles at 1 mg/mL concentration was adjusted to 11 with concentrated ammonia. To this solution, 10 mg of silane-PEG-COOH was added and the reaction was allowed to proceed for 24 hours with shaking. The resulting nanoparticle solution was heated at 80° C. for 2 hours in order to achieve covalent linkage between polymer chains and the particle surface. Finally, the resulting functionalized nanoparticles (Fe$_3$O$_4$@silane-PEG-COOH) were centrifuged at 4000 rpm for 10 min using Amicon® Ultra-15 centrifugal filters. The concentrated product (termed NS—COOH in FIG. 1) was stored at 4° C.

Analysis of Functional Groups on Nanoparticles

Fluorescence labeling was used to quantify functional groups on nanoparticle surfaces because of its high sensitivity. All labeling reactions are performed in dark at room temperature. To determine the number of amines on the nanoparticle surface Alexa Fluor® 488 NHS ester (Invitrogen, Carlsbad, Calif.) was used. Fe$_3$O$_4$@silane-PEG-NH$_2$ nanoparticles were reacted with 10 molar excess of dye for 2 hours. Following the labeling reaction, the sample was dialyzed against PBS using a 2000 Da MW cut-off membrane to remove unbound fluorescent molecules. All the fluorescence measurements (excitation 480 nm, emission 520 nm) were performed on fluorescence plate reader (Synergy HT; BioTek Instruments, Winooski, Vt.). The fluorescence intensity of the sample was compared to a standard curve. The iron concentration was measured using ICP-OES after digesting all samples with concentrated HNO$_3$ acid and nanoparticle concentration was calculated assuming that each particle was made of Fe$_3$O$_4$ and a 5.2 g/cm$^3$ density.

To determine the number of carboxyl groups on the nanoparticle surface, Alexa Fluor® 488 Cadaverine dye was used. First a mixture of EDC:N-hydroxysulfosuccinimide (sulfo-NHS) was added to Fe$_3$O$_4$@silane-PEG-COOH nanoparticle solution and allowed to react for 15 minutes to activate carboxyl acid groups. Then 10 molar excess Alexa Fluor® 488 Cadaverine dye was added and allowed to react overnight. Finally the product was dialyzed against PBS using a 2000 Da MW cut-off membrane to remove unbound fluorescent molecules. All the fluorescence measurements (excitation 493 nm, emission 516 nm) were performed on fluorescence plate reader (Synergy HT; BioTek Instruments, Winooski, Vt.). The fluorescence intensity of the sample was compared to a standard curve. The iron concentration was measured using ICP-OES after digesting all samples with concentrated HNO$_3$ acid and nanoparticle concentration was calculated assuming that each particle was made of Fe$_3$O$_4$ and a 5.2 g/cm$^3$ density.

The resultant parent SPIO exhibits a core size of ~17 nm (TEM). Upon surface modification with silane-PEG-NH$_2$ or silane-PEG-COOH, the hydrodynamic size of the SPIOs is 50 and 35 nm (s.d.=5) for the NS—NH$_2$ and NS—COOH particles, respectively (based on DLS measurement). Further, the NS—NH$_2$ particles contained ~200 amine groups per particle compared to 500 carboxyls for NS—COOH.

Synthesis of Short Linear Nano-Constructs

Synthesis and Characterization of Linear Nano-Constructs (LNS)

LNS particles were synthesized using the following protocol. First each mono-functionalized nanoparticles (Fe$_3$O$_4$@silane-PEG-COOH and Fe$_3$O$_4$@silane-PEG-NH$_2$) in water were transferred to organic phase. The concentrated samples of functionalized nanoparticles were added to DMF (dimethylformamide) and heated to evaporate all water. The concentrations of nanoparticles were then adjusted to 1 mg/mL by adding more DMF. To activate carboxyl groups on Fe$_3$O$_4$@silane-PEG-COOH nanoparticles, catalytic amount of pyridine and 50 molar excess DCC (N,N'-Dicyclohexylcarbodiimide) relative to the available COOH groups were added and allowed to react for 30 minutes. To this reaction mixture 2.5 excess Fe$_3$O$_4$@silane-PEG-NH$_2$ nanoparticles (relative to number of Fe$_3$O$_4$@ silane-PEG-COOH nanoparticles) was added and shake for another 30 minutes. At this time point, the reaction was arrested by 'deactivating' the carboxyl groups. To deactivate carboxyl groups, 10 molar excess ethylenediamine (relative to the number of carboxyl groups available) was added and shake for another 30 minutes. Finally, 10 times excess distilled water (relative to the volume of DMF) was added to the above reaction mixture. LNS particles were separated by centrifugation with Amicon® Ultra-15 centrifugal filters.

Magnetic Separation of LNS Particles

To separate NC's from the parent nanoparticles a powerful magnet was used. Briefly, as synthesized NC's at the concentration of 10 mg/mL were transferred to a small test tube and were exposed to a powerful magnetic field for 90 minutes. NC's attached at the walls of the test tube were then collected separately and stored at 4° C.

Modification of LNS Particles with Targeting Ligand

The cyclo (Arg-Gly-Asp-D-Phe-Cys) or c(RGDfC) was conjugated onto NC's via maleimide chemistry. First, amine-functionalized NC's in PBS were vortexed with 10 molar excess sulfo-SMCC (sulfosuccinimidyl 4-(N-maleimidomethyl)cyclohexane-1-carboxylate) for 15 minutes. Next, 5 molar excess (relative to the number of amines on NC's) of c(RGDfC) was added and allowed to react for 2 hours. The product was dialyzed against PBS using a 2000 Da MW cut-off membrane to remove unbound RGD molecules.

Bio-Rad DC protein assay was used to quantify the RGD on NC's. Briefly, 200 µL of Bio-Rad dye solution (1 part of commercially available Bio-Rad was diluted with 2 parts of distilled water and filtered through a whatman filter) was added to 800 µL of 10 mg/mL NC's and vortexed. The absorbance of the sample was obtained at 595 nm after incubating the sample for 15 minutes. The absorbance value was compared to a standard curve which was obtained by measuring the absorbance of known concentrations of RGD with Bio-Rad dye solution.

Detailed analysis of TEM images (FIG. 1B) showed that the method resulted in Linear Nano-Structure particles primarily composed of 3-5 parent iron oxide nanospheres (length of ~100 nm) with a high yield of >70% (based on the starting nanospheres).

Example 2

In this example, we show iron oxide nanochains can be used to hard-to-reach selected glioblastoma multiforme (GBM), an invasive brain cancer. GBMs are characteristically diffuse and invasive with infiltrating edges and distant glioma cell dispersion. In addition to the non-localized topology of glioma cells, targeting molecules and nanoparticles into brain tumors is challenging due to the blood-brain barrier (BBB). To evaluate the targeting efficiency of nanochains, we decorated the nanoparticle with a ligand that targets an overexpressed biomarker found on the remodeled endothelium of brain tumors. The remodeled endothelium associated with brain tumors and its surrounding microenvironment offers a diverse set of targetable biomarkers, which differs from that of healthy vascular beds. Overall, our targeting strategy was based on two important design criteria: (1) the size and the multi-valent avidity, due to formation of multiple receptor-ligand bonds, makes nanoparticles ideal for targeting of vascular-associated pathologies, and (2) the oblong-shaped nanochain possesses a unique ability to seek and rapidly deposit on the blood vessels of glioma sites via vascular targeting. Using mouse models of GBM and histological analyses, we show that nanochains achieved superior deposition at primary and invasive sites of GBM when compared to their spherical nano-particle counterparts. Considering the hard-to-reach nature of gliomas, the very high intratumoral levels of iron oxide facilitated MR imaging with precise demarcation of glioma sites including locations with dispersing glioma cells.

EXPERIMENTAL SECTION

Synthesis of Parent Iron Oxide Nanospheres

Iron oxide nanoparticles were synthesized by the co-precipitation of Fe(II) and Fe(III) ions in the presence of sodium hydroxide solution. The surface of the iron oxide nano-particles was modified with PEG (2 kDa) using silane-PEG-COOH or silane-PEG-NH2.

Synthesis of Nanochains

First, each mono-functionalized nanoparticles (IONP-COOH and IONP-NH2) were transferred from water to organic phase. The concentrated samples of functionalized nanoparticles were added to dimethylformamide (DMF) and heated to evaporate all water. The concentrations of nano-particles were then adjusted to 1 mg mL$^{-1}$ by adding more DMF. To activate carboxyl groups on the IONP-COOH nanoparticles, catalytic amount of pyridine and 50 molar excess N,N'-dicyclohexyl-carbodiimide (DCC) relative to the available COOH groups were added and allowed to react for 30 minutes. To this reaction mixture 2.5 excess IONP-NH$_2$ nanoparticles over the number of IONP-COOH nanoparticles was added and shaken for another 30 minutes. At this time point, the reaction was arrested by 'deactivating' the carboxyl groups. To deactivate carboxyl groups, 10 molar excess ethylenediamine (relative to the number of carboxyl groups) was added and shaken for another 30 minutes. Finally, 10 times excess distilled water (relative to the volume of DMF) was added to the above reaction mixture. Nanochain particles were separated by centrifugation with Amicon® Ultra-15 centrifugal filters. To further clean nanochains from any unreacted parent nanoparticles, a strong magnet was used. Briefly, synthesized nanochains at a concentration of 10 mg mL$^{-1}$ were transferred to a small test tube and were exposed to a powerful magnetic field for 90 minutes. Nanochain particles attached at the walls of the test tube were then collected and stored at 4° C.

Functionalization of Nanochains with Targeting Ligand

The CREKA peptide was conjugated onto the particles via maleimide chemistry. First, amine-functionalized nanochains in PBS were vortexed with 2 molar excess sulfosuccinimidyl 4-(N-maleimidomethyl)cyclohexane-1-carboxylate (sulfo-SMCC) for 15 minutes. Next, CREKA was added at a 5 molar excess over the number of amines on nanochains and allowed to react for 2 hours. The product was dialyzed against PBS using a 100 000 Da MW cut-off membrane to remove unbound peptide.

The number of CREKA per nanochain particle was determined by the measurement of collected free CREKA solution after separation using a desalination column. The concentration of CREKA was determined using a high-performance liquid chromatography (LC) system with an analytical column (250 mm×4.6 mm, pore size 5 micron, Luna-C18). An isocratic elution technique was used where the mobile phase contained a mixture of solvent A (0.1% trifluoroacetic acid in water) and solvent B (50% acetonitrile solution and 50% methanol) (A:B 20:80, v/v). The flow rate was set at 1.0 ml min$^{-1}$. The sample injection volume was 50 µL, and the detector wavelength was 220 nm.

Tumor Models

All animal procedures were conducted under a protocol approved by the IACUCs of Case Western Reserve University and Cleveland Clinic. For the CNS-1 rodent glioma tumor model, 5-8-week-old athymic nude mice (~25 g) were housed in the Athymic Animal Core Facility at Case Western Reserve University according to institutional policies. CNS-1 cells were infected with green fluorescent protein (GFP) encoding lenti-virus, harvested for intracranial implantation by trypsinization, and concentrated to 1×10$^5$ cells per µL in PBS. Mice were anesthetized by intraperitoneal administration of ketamine and xylazine and fitted into a stereotaxic rodent frame. Cells were implanted at AP=+0.5 and ML=−2.0 from bregma at a rate of 1 µL min$^{-1}$ in the right striatum at a depth of −3 mm from dura. A total of 200 000 cells were implanted per mouse. Similar procedures were employed for the human T4121 glioma model. For more details about the human GBM specimen and derivative glioma stem cells, see additional methods in ESI.†

Histological Evaluation

Immunohistochemistry was performed to evaluate the topology of fibronectin expression with respect to glioma cells and blood vessels. The mice were anesthetized with an IP injection of ketamine/xylazine and transcardially perfused with heparinized PBS followed by 4% paraformaldehyde in PBS. Brains were explanted and post-fixed overnight in 4% paraformaldehyde in PBS. The tissues were soaked in 30% sucrose (w/v) in PBS at 4° C. for cryosectioning. Serial tissue sections of 12 µm in thickness were obtained. Direct fluorescence of GFP (green) imaging was performed for imaging the location of glioma cells. To visualize the tumor microvasculature and fibronectin, the tissue slices were immunohistochemically stained for the endothelial antigen CD31 or anti-fibronectin primary antibody (BD Biosciences, Pharmingen). The tissues were also stained with the nuclear stain DAPI. The tissue sections were imaged at 5, 10 or 20× on the Zeiss Axio Observer Z1 motorized FL inverted microscope. To obtain an image of the entire large tissue section (i.e., entire brain section), a montage of each section was made using the automated tiling function of the microscope.

MR Imaging

MR images were acquired on a 7 T Bruker MRI system. A volume coil (3.5 cm inner diameter) was employed. The sequence used was a Rapid Acquisition with Relaxation Enhancement (RARE). High-resolution images were obtained before and 60 min after IV injection of the nano-chains (at a dose of 10-20 mg Fe per kg b.w.) using a T2-weighted RARE sequence with the following parameters: TR/TE=3646.6/31 ms, matrix=256×256, FOV=3×3 cm, and 5 averages. The acquisition time was 9 minutes 43 seconds. This resulted in an in-plane spatial resolution of 111.7 µm and a slice thickness of 0.5 mm.

3D Cryoimaging

After the entire brain was harvested, they were preserved in 4% paraformaldehyde, soaked in 30% sucrose in PBS, and frozen in OCT. The BioInVision CryoViz was used to section through each brain in slices of 25-µm thickness, while bright-field and fluorescence images of each tissue section were collected at 1.25× magnification. Using CryoViz software, a 3D visualization was created for the bright-field organ view as well as a corresponding 3D visualization of the distribution of GFP glioma cells in the brain. Sub-sampling in 3D reconstruction created the final images with a voxel size of 10.418×10.418×50 µm. To reflect visually distinguishable signal, a maximum intensity projection of the green signal in the fluorescent acquisition image was obtained and thresholded. This image was overlaid with the 3D bright-field reconstruction of the brain.

Statistical Analysis

Means were determined for each variable in this study and the resulting values from each experiment were subjected to one-way analysis of variance with post hoc Bonferroni test (SPSS 15, Chicago, Ill.). A P value of less than 0.05 was used to confirm significant differences. Normality of each data set was confirmed using the Anderson-Darling test.

Results and Discussion

Fabrication of Nanochains

Figure 2:
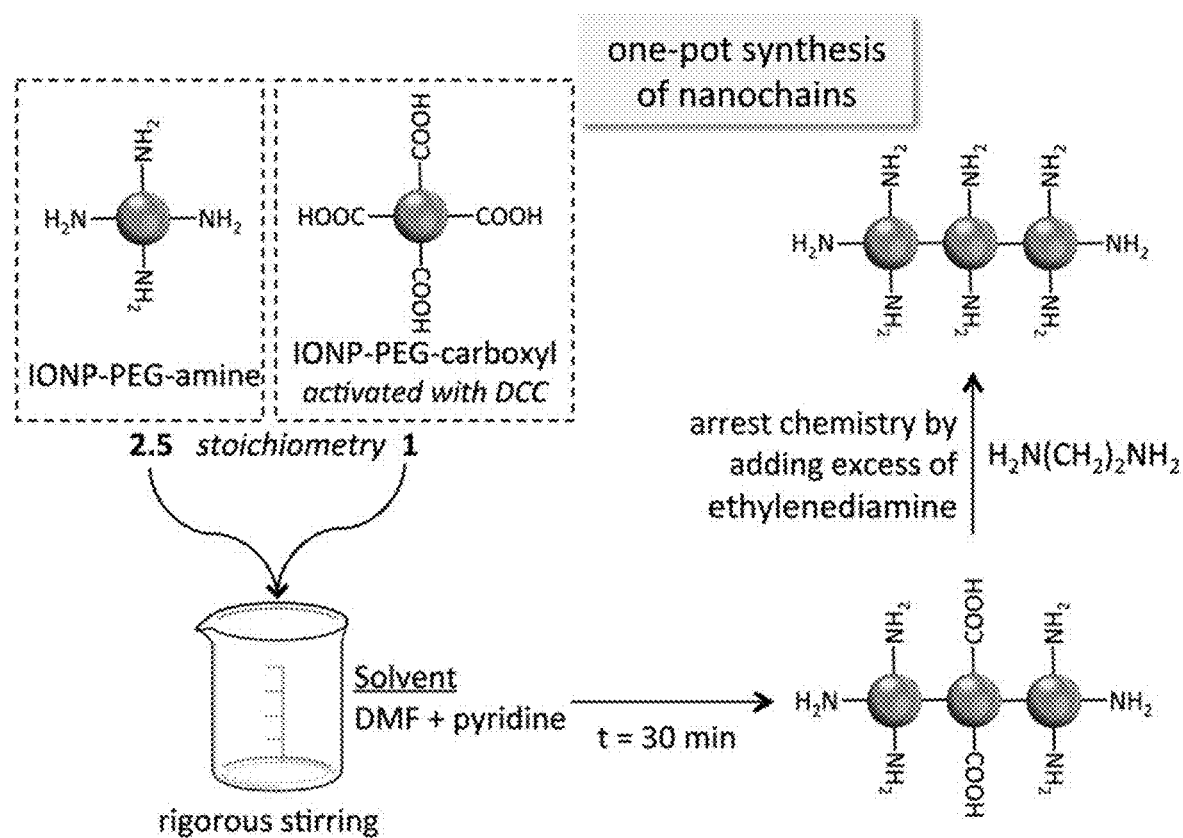
FIG. 2 is a reaction scheme of the synthesis of iron oxide nanochains.

The synthetic process is shown in FIG. 2 using iron oxide nano-particles (IONP) as the parent particles. First, the IONP-COOH and IONP-NH2 were transferred from water to organic phase. The particle concentration for both IONP suspensions was then adjusted to 1 mg mL$^{-1}$. In the nano-chain formation reaction, DCC acted as the activating agent of the carboxylic acid groups on the surface of IONP-COOH. The IONP suspension was added to dimethylformamide (DMF) and heated to evaporate water before adding DCC, because the activation efficiency of DCC is very high in anhydrous solutions. After 30 minutes, IONP-NH$_2$ particles were added at a particle ratio of 2.5:1 (IONP-NH$_2$: IONP-COOH) under rigorous stirring. During the nanochain formation reaction, the activated leaving groups on IONP-COOH are displaced by terminal amines of IONP-NH$_2$ nanoparticles. The reaction was allowed for 30 min. To arrest the reaction, the rest of the leaving groups are displaced by ethylenediamine. Following cleaning steps with water, the nanochains were separated from unreacted parent IONP using magnetic separation for 90 min. As shown in FIG. 3A, DLS measurements show the hydrodynamic sizes of the parent IONP and the final nanochain. It can be seen that the distributions of the parent particles disappear and a new peak appears, representing the population of nanochain particles. Considering the size distributions of the starting particles, the nanochain's size indicates chain-like particles consisting of 3-5 IONP members. TEM images confirm the structure and number of constituting IONP in the nanochains (FIG. 3B). Further, the yield of the synthetic process is very high and consistent. Analysis of TEM images indicates that the majority of the parent IONP particles are incorporated in chain-like structures. Notably, the size of the nanochains remained unchanged over 30 weeks (FIG. 3C). Finally, T2 relaxometry measured the T2 relaxivity of the nano-chains to be 103.2 s$^{-1}$ mM$^{-1}$. Table 1 summarizes some of the characteristics of the particles.

TABLE 1

Summary of nanoparticle characteristics

| | Hydrodynamic size (mean ± s.d.) | Number of functional groups | Fe content per 1 mg |
|---|---|---|---|
| IONP—NH2 | 43.4 ± 2.3 nm | 200 (amines) | 52% |
| IONP—COOH | 33.2 ± 3.2 nm | 500 (carboxyls) | 43% |
| Nanochain | 121.1 ± 33.4 | 700 (amines) | 51% |

In addition to iron oxide nanochains, our synthetic method offers great flexibility to employ other types of starting nano-particles composed of different material. As an example, we describe the synthesis of gold nanochains in the ESI.

In conclusion, two mono-functionalized nanoparticles (i.e., amine and carboxyl) were mixed at a specific stoichiometry and allowed to react for a well-defined finite time. The formed nanochains were then separated by centrifugation and magnetic separation. Other synthetic approaches have resulted in nanochain particles. For example, we previously reported the synthesis and biomedical applications of chain-like nano-particles using an elegant but multifaceted method. To assemble nanochains, the previous method was based on a stepwise solid-phase chemistry approach. Briefly, nanospheres were introduced in the resin in a step-by-step manner followed by multiple washing cycles for each step. The new one-pot method is significantly simpler and highly efficient (yield >90%).

Histological Evaluation of the Vascular Target

Nanoparticles are capable of targeting brain tumors via highly specific vascular targeting of the vascular bed associated with the primary tumor mass and its invasive sites. Notably, the remodeled endothelium associated with brain tumors and its surrounding microenvironment offers a diverse set of targetable biomarkers. For example, vascular targets over-expressed in gliomas include αvβ3 integrin, platelet-selectin (P-selectin), vascular endothelial growth factor receptors (VEGFR) and fibronectin. In particular, we were interested in fibronectin due to its role in migration of glioma cells. Most importantly, overexpression of fibronectin is strongly associated with the perivascular regions of GMB tumors. In addition to its selective perivascular expression, fibronectin is abundant and plays a critical role in migrating and invasive glioma cells. Considering its insignificant expression on the endothelium of normal tissues, fibronectin is an ideal fit to our vascular targeting scheme.

To confirm the availability of fibronectin as a vascular target, we performed histological analysis using the orthotopic CNS-1 glioma model in mice. In terms of pathological and genetic similarities to the human disease, the CNS-1 model is one of the few rodent models that recapitulate the microenvironment of the human disease and displays several histological features and diffuse growth and invasive pattern similar to human GBM. In addition to their ability to express several glioma markers, a three-dimensional cryoimaging technique showed that the rodent CNS-1 glioma cells is a valid system to study the highly dispersive nature of glioma tumor cells along blood vessels and white matter tracts in vivo.

Animals were euthanized 8 days after orthotopic inoculation of CNS-1 cells, which were infected with GFP encoding lentivirus. The brains were collected for histological analysis of brain tumor location (CNS-1-GFP cells). Using fluorescence microscopy, images of entire histological sections of the organs were obtained at a low magnification (5×) using the automated tiling function of the microscope. FIG. 4 shows a representative image of the entire left hemisphere of a brain displaying the location of the primary tumor and presence of clusters of invasive glioma cells dispersed in the brain parenchyma. Notably, abundance of fibronectin was seen in the primary tumor (FIG. 4B) as well as invasive sites (FIG. 4C).

Further, we assessed the location of glioma cells with respect to blood vessels and the associated presence of fibronectin. Blood vessels associated with the primary and invasive glioma sites presented a remodeled endothelium as indicated by the abundance of fibronectin (FIG. 4C). It should be noted that no fibronectin can be seen in healthy brain tissues, which indicates that it is a highly selective vascular target associated with GBM sites.

Quantitative Evaluation of Targeting Brain Tumors

To target the glioma-associated endothelium, we employed the fibronectin-targeting peptide CREKA, which has been shown to specifically bind fibrin fibronectin complexes in tumors with very high specificity. The CREKA peptide was conjugated onto the available amines on the surface of the nanochains using the heterobifunctional cross-linker sulfo-SMCC. An HPLC assay was used to quantify the number of CREKA peptides per nanochain particle, confirming that all the 700 amines available for conjugation were consumed.

Animals were systemically injected with nanochains 8 days after orthotopic inoculation of the CNS-1 cells. Each dose contained 4-10 mg of iron per kg of body weight, which corresponded to $1.6 \times 10^{14}$ nanochain particles being administered to each animal. The concentration of the nanochains in tissues was quantified by direct measurement of iron ex vivo. To determine the time course of the intratumoral deposition of CREKA-targeted nanochains, animals were euthanized at 0, 1 and 8 hours post-injection (n=5 mice per time point). Whole brains were perfused and tissues were homogenized. The iron concentration in the homogenate was directly measured ex vivo using ICP-OES. Tumor-bearing mice injected with saline were used for correction of the background levels of iron in the tumor tissue. FIG. 5A shows the intratumoral deposition of nanochains reaches very high levels quickly within 1 h after injection. In fact, vascular targeting of the nanochains is rapid as the later time point indicates (t=8 h). The number of nanoparticles that successfully targeted glioma sites corresponded to a significant portion of the injected dose (3.7% as shown in FIG. 5B). Using the same methodology, we quantitatively compared the CREKA-targeted nanochains to their non-targeted variant and a CREKA-targeted nanosphere based on the parent IONP. All formulations were administered at a dose containing an equal number of particles per kilogram of body weight. At t=1 h after injection, the tumor deposition of the targeted nanochain was ~2.6-fold higher than its nontargeted variant and the targeted nanosphere. This indicates that the oblong shape and flexibility of the chain-like nanoparticle enhanced its vascular targeting capabilities.

Typically, brain tumors are nearly inaccessible to most molecules due to poor penetration across the blood-tumor barrier (BTB). Notably, nanoparticles have shown promise, because they can "squeeze" into intracranial tumors through their leaky vasculature due to the enhanced permeation and retention (EPR) effect. For example, it was demonstrated in patients with GBM that long circulating liposomal nanoparticles could penetrate the BTB. Furthermore, contrast enhancement of GBMs in CT and MR imaging has generated controversy as to whether the BTB barrier presents significant limitations to drug delivery. Many studies have shown that while the blood-brain barrier (BBB) is partially breached resulting in an increased penetration of drugs into brain tumors compared to normal brain, BBB is still present in GBMs, which consist of blood vessels that are not as leaky as the angiogenic vessels observed in other cancer types. This results in low penetration of nanoparticles into the brain tumor interstitium with a patchy, near-perivascular distribution, resulting in failure to reach the majority of the primary tumor mass and especially its invasive sites. Furthermore, the EPR effect is typically noticeable at the primary regions of GBM, while it is attenuated at the invasive sites of brain tumors with dispersing cancer cells. This is due to the fact that the BBB of invasive sites has a very high likelihood to remain intact. Most importantly, it is not uncommon to find dispersing brain tumor cells as far away as 4 cm from the primary site.

Contrary to EPR-driven passive targeting or deep-tissue active targeting, vascular targeting of nanoparticles to GBMs is a very attractive strategy. Fibronectin and fibrinogen are not innate brain matrix proteins. However, the endothelium and perivascular regions of tumors contain high levels of products of blood clotting. Fibrin based proteins typically arise due to systemic intervention upon injury to the endothelium. A fibrin meshwork is initially formed by conversion of fibrinogen, which leaks into tumor via its leaky endothelium. Plasma fibronectin becomes covalently linked or otherwise bound to the fibrin meshwork. These fibrin fibronectin complexes on the tumor endothelium are targetable by CREKA-decorated nanoparticles. Further, fibronectin plays a key role in the migration of glioma cells. Our histological analysis confirmed the abundance of fibronectin in two GBM models in mice. Thus, the remodelled endothelium associated with glioma cells served as an ideal targetable site of the disease, which accurately reflected the changes that occurred behind the vascular bed in the interstitium.

In this context, due to its size, one nanoparticle can be decorated with a high number of targeting ligands, which results in the formation of multiple receptor-ligand bonds. This geometrically enhanced multivalent avidity makes nano-particles ideal for targeting vascular biomarkers. Besides blood components, the endothelium is the closest point-of-contact for blood circulating nanoparticles. Thus, by having direct access to the vascular bed, nanoparticles continuously scavenge the endothelium for the vascular bio-markers associated to brain tumors. An additional benefit of nanoparticle technology is that adjusting the shape can significantly dictate targeting avidity. Not surprisingly, the oblong shape and flexibility of the nanochains resulted in superior deposition at glioma sites when compared to their spherical counterparts. We have previously seen that chain-like nano-particles exhibit similar organ distribution to their spherical counterparts and end up in organs of the reticuloendothelial system. The safety profile of the nanochain particles is part of ongoing short and long-term toxicity studies.

Imaging of Invasive Brain Tumors Using MRI

To explore the in vivo performance of the new nanochains, we explored the ability of iron oxide nanochains to target the hard-to-reach invasive brain tumors for imaging and diagnostic applications. Treatment options for GBM typically involve surgery and radiation, with the addition of temozolomide based chemotherapy for glioma patients.

Despite advancements, the recurrence of glioma is >90%. This stems from the invasive nature and blood-brain barrier (BBB) limiting the effectiveness of surgery and systemic chemotherapy, respectively. Thus, radiation is an essential part of the tumor treatment protocol. However, a major limitation for successful radiotherapy is the lack of accurate image guidance and exact topology of the disease.

Figure 6A:
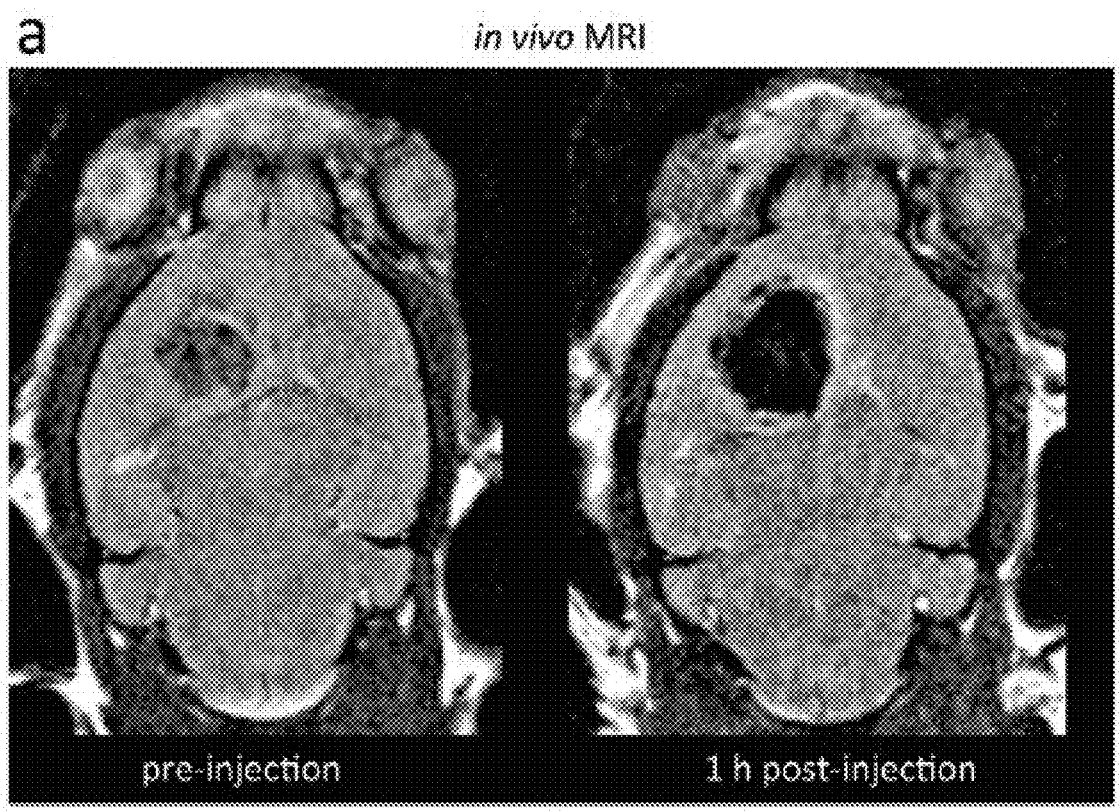
FIGS. 6A-C illustrate representative in vivo MR images of the brain of mice bearing orthotopic glioma CNS-1 tumors using a 7 T MRI. (A) Coronal T2-weighted images of the brain of a mouse before and 1 h after injection of CREKA-targeted nanochains. (B) In the 1 h post-injection MR image, the signal enhancement was thresholded and color-coded in blue (left). In the end of MR imaging, the brains of the animals were perfused, excised, and imaged ex vivo using 3D cryo-imaging. 3D cryo-imaging provided an ultra-high-resolution fluorescence volume of the brain showing the topology of CNS-1-GFP cells. The in vivo MR image (left) and the ex vivo fluorescence image (right) show the colocalization of MR signal and glioma cells. (C) The absolute MR signal intensity in gliomas and the healthy brain was measured in manually drawn ROIs. The signal intensity in glioma sites was normalized to the signal of the corresponding healthy brain region (scale: 0-1). Since lower values indicate greater contrast in T2 images, normalized intensity values of 0 and 1 correspond to maximum and minimum contrast, respectively (data presented as mean±standard deviation; n=5; *P<0.05).
Figure 6B:
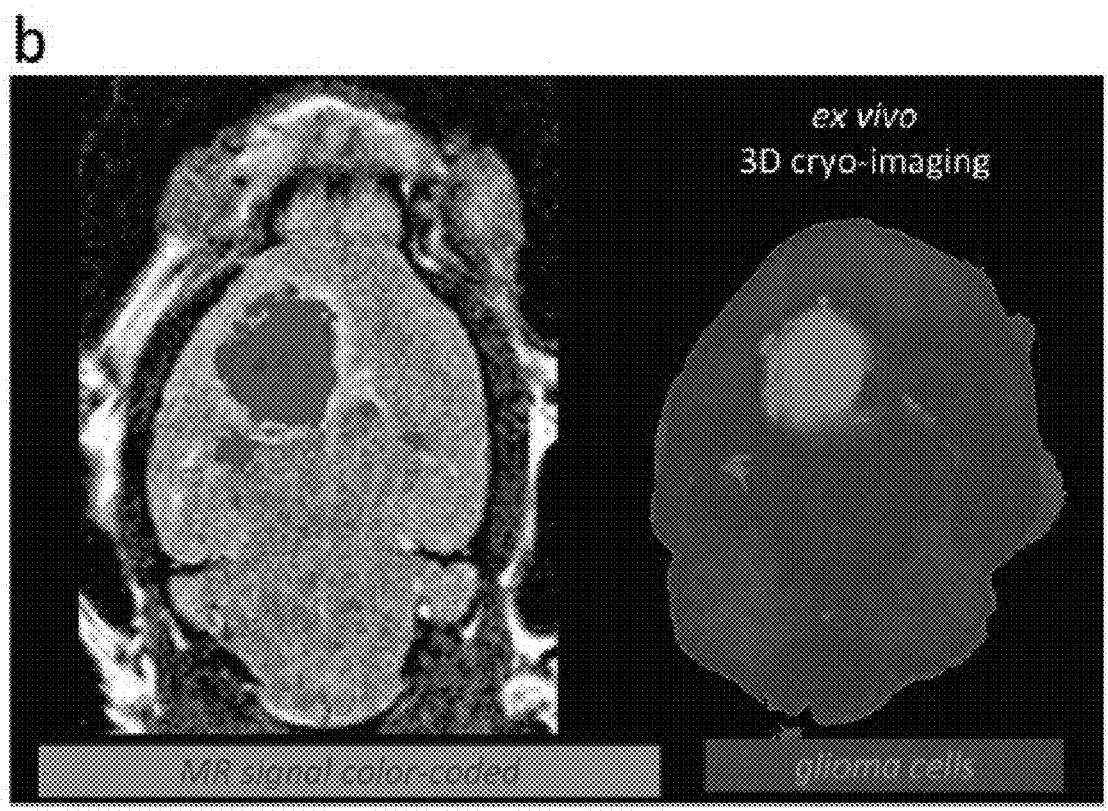
Figure 11:
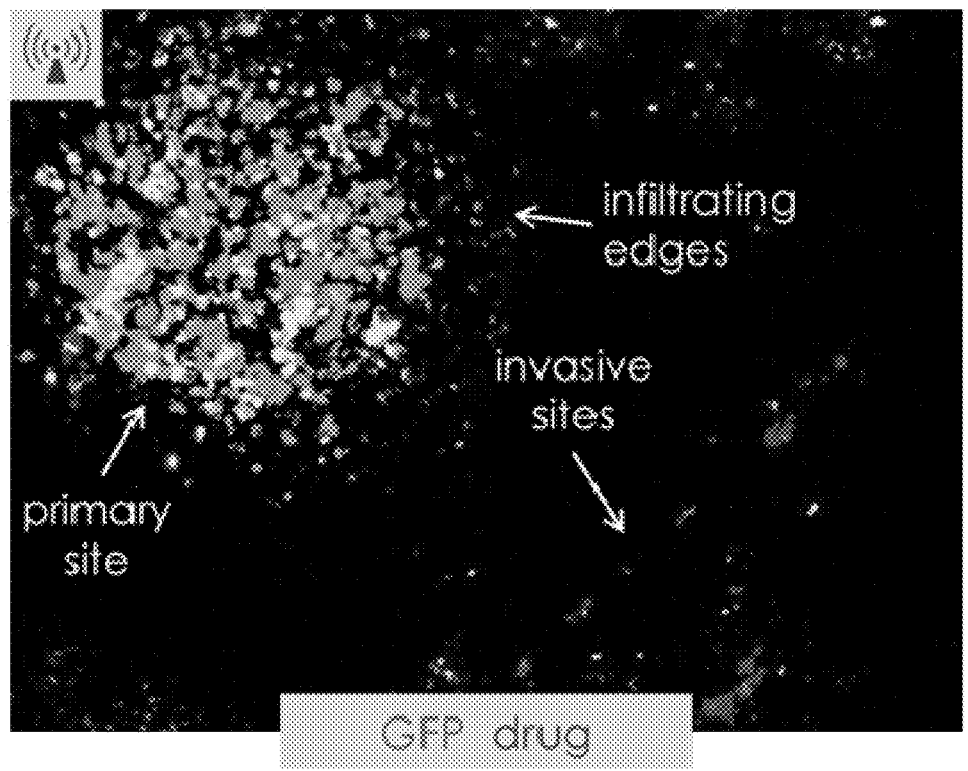
FIG. 11 illustrate an image showing histologic evaluation of an MPNC-I treatment. Histological evaluation of the anticancer effect of nanochains was performed in the orthotopic GBM2 model (human glioma) in mice [magnification, ×5; green, glioma cells (GFP); red, doxorubicin]. Fluorescence imaging of an entire histologic section of the brain shows the primary tumor, and its infiltrating edges and invasive sites (arrows). Fluorescence imaging of the same histologic section shows the widespread distribution of doxorubicin molecules after a 60-min application of RF (5 mT, 20 kHz). It should be noted that very low levels of drug are observed in the absence of RF application with the drug being distributed primarily in the periphery of the primary site (images not shown).

FIG. 11 shows representative coronal T2-weighted images of mice with orthotopic CNS-1 tumors (n=5) obtained using a 7 T MRI before and after administration of the CREKA-targeting nanochains (at a dose of 20 mg Fe per kg b.w.). This is a typical dose of IO nanoparticles used in imaging small animals with MRI (e.g., 10 mg Fe per kg). 45 MR images were acquired a few minutes prior to injection of the agent and 60 min after injection. The MR parameters in the pre- and post-injection images were identical. FIG. 6A compares the pre-injection and 1 h post-injection images of the brain of the same animal. Due to effective vascular targeting of the nano-chains, a significant negative contrast was observed in the post-injection image highlighting the periphery and the core of the primary site. Most importantly, infiltrating edges and invasive sites were also clearly marked (FIG. 6B, left panel). To confirm the accuracy of the in vivo MR imaging, terminal analysis was employed. At the end of the last in vivo imaging session, the animal was euthanized and the brain was per-fused, collected and prepared for 3D cryo-imaging. Serial cryo-sections of entire brains were obtained using 3D reconstructions, providing ultra-high-resolution fluorescence images and the location of primary and invasive glioma sites (i.e., CNS-1-GFP). The in vivo MR image and the ex vivo fluorescence image (FIG. 11B, right panel) confirm the targeting accuracy of the nanochain as indicated by the colocalization of MR signal and glioma cells.

Figure 6C:
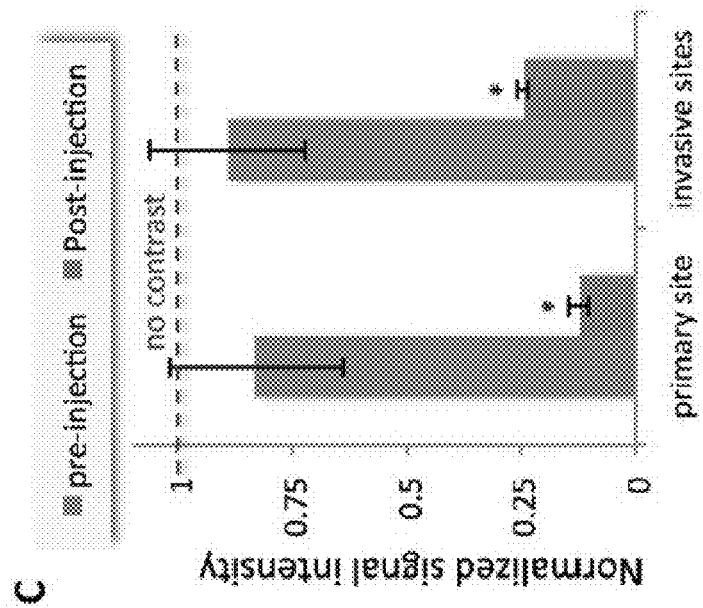

The ability of the nanochains to target invasive GBM was evaluating by quantitatively analyzing the MR signal intensity (FIG. 6C). The absolute MR signal intensity in primary and invasive glioma sites and the corresponding healthy brain tissues was measured using manually drawn regions of interest. By normalizing the tumor signal to that of corresponding healthy tissues, the normalized signal intensity had a scale of 0-1 with lower values indicating greater contrast in T2 images. A normalized intensity value of 1 corresponds to no contrast compared to healthy tissue. The pre-injection image exhibited values for both the primary and invasive glioma sites that were fairly similar and statistically close to 1. However, precise targeting of the nanochain to glioma sites generated a significantly high negative contrast. In the post-injection images, the primary and invasive glioma sites exhibited a normalized intensity value of 0.12 and 0.24 respectively, indicating significantly higher contrast compared to the post-injection background signal of the healthy or uninvolved regions of the brain.

Example 3

Synthesis of Higher-Order Multi-Particle Nanoconstructs (MPNC)

500 µL of carboxyl modified liposomes at the concentration of $3 \times 10^{14}$ were reacted with 3.8 mg of EDC and 4.3 mg of sulfo-NHS in PBS (100 uL) for 15 minutes. To this solution LNS nanoparticles in PBS at the concentration of $3 \times 10^{13}$ were added and shake overnight. The product was purified by dialysis against PBS using a 2000 Da MW cut-off membrane. The purified product was exposed to a powerful magnetic field for 90 minutes to separate unbound LNS particles from the desired MPNC-I particle (FIG. 7).

Results

The higher-order MPNC particles have been characterized in terms of their size, structure, iron content and drug stability using Dynamic Light Scattering, Transmission Electron Microscopy, ICP-OES and drug leakage studies, respectively. For example, the analyses showed that the fabrication method of MPNC particles is highly reliable and consistent. Using remote loading techniques, the 30-nm liposome component of the MPNC-I particles was loaded with doxorubicin or vincristine. Composition analysis has shown that 1 mL of the formulation contains 5 mg of iron, 1.67 mg of doxorubicin, or 0.7 mg of vincristine. It should be noted that the drug encapsulation is highly stable and consistent with parent liposomal formulations. Further, functionalized of the MPNC particles with cRGD peptides resulted in ~2,300 targeting ligands per particle.

Example 4

Linear Nano-Constructs Using Gold or Silica Nanospheres

In addition to iron oxide nanoparticles, our synthetic method exhibits an enormous flexibility to use other types of nanoparticles composed of different material. Here, we provide examples with gold or silica being the starting nanospheres.

Synthesis and Characterization of Linear Nano-Constructs (LNS)

Gold or silica nanoparticles were synthesized using established methods. For instance, gold nanoparticles (AuNP) were synthesized using the Brust-Schiffrin method with some modification. Briefly, $HAuCl_4$ solution (367 µL) and tetraoctylammonium bromide (TOAB, 0.1367 g) were dissolved in toluene at room temperature. Dodecylamine (0.112 g) was added and stirred at room temperature for 10 min. A reducing agent, $NaBH_4$ solution in ice-cold water was added slowly in to the reaction mixture. Following the addition of $NaBH_4$, the solution turned from orange to wine red solution. The resulting AuNP were precipitated with ethanol, centrifuged at 6,000 rpm for 15 min, and dried under nitrogen for 30 min. Upon dissolving the nanoparticles in chloroform, SH-PEG-$NH_2$ or SH-PEG-COOH was added in large excess and allowed to react for 2 days at room temperature. Chloroform was removed by air-drying.

By using different stoichiometric ratios between the two starting particles (e.g., 1.5:1, 2.5:1, 3.5:1) and reaction times (e.g., 10, 30, 60 min), one can control the composition of the resultant chains in terms of their lengths. FIG. 8 illustrates three different conditions resulting in different designs indicating the control of our method over the length of the nanochains. Instead of magnetic separation that we used in the case of iron oxide particles, we use here centrifugation to fractionate the chains into starting spheres, small chains (dimers and trimers) and larger chains (tetramers and pentamers).

Example 5

RF-Triggered Drug Release

Radiofrequency (RF) field was generated from a custom-made solenoid RF generator (5 mT magnetic field and 20 kHz frequency were used) to trigger drug release in vitro. The MPNC particles were exposed to different RF conditions and exposure times (e.g., 15, 30, 60, 90 and 120 min). The released drug concentration was measured using dialysis followed by quantitative HPLC assays. A representative sample of the data is shown in FIG. 4, indicating that the release rate of two different drugs from the particles was similar.

Organ Distribution and Targeting Studies

Figure 10:
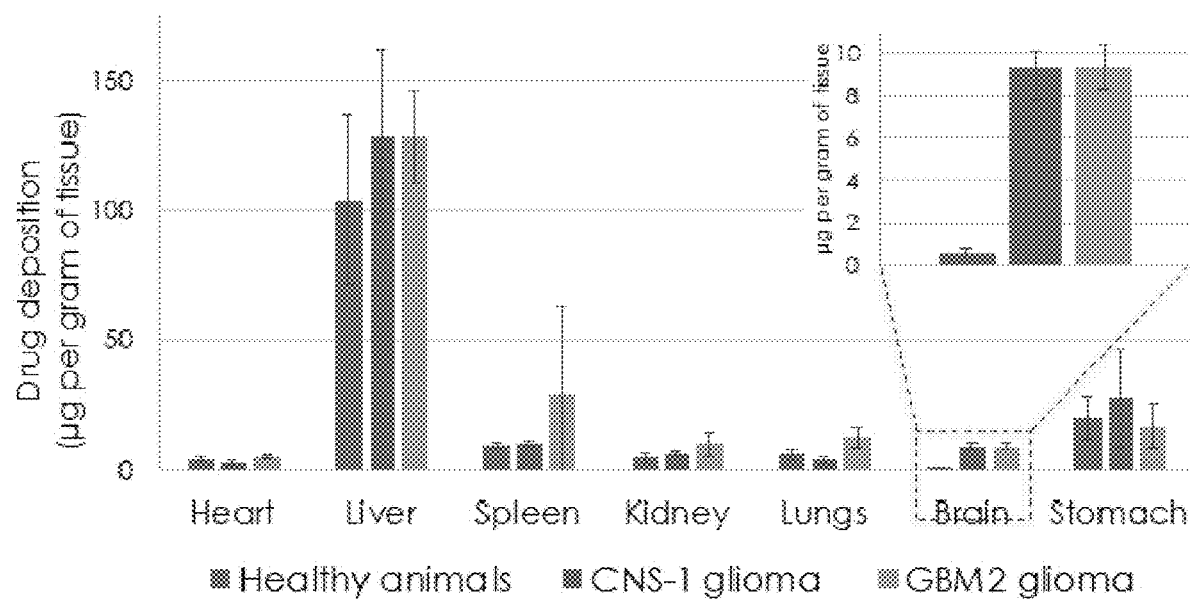
FIG. 10 illustrates a graph showing organ distribution of nanochains and glioma targeting efficacy. The nanochains were injected IV in three groups of animals including healthy mice, and mice with orthotopic CNS-1 and GBM2 glioma tumors (n=4 per group). The animals were transcardially perfused with heparinized PBS 24 hours after intravenous administration, and brains were retrieved and analyzed for doxorubicin content following an established protocol. At this time point, doxorubicin was undetectable in blood circulation.

The organ distribution of integrin-targeting MPNC particles was evaluated in healthy mice (n=4), human glioma model (GBM2) and rodent glioma model (CNS-1) at 24 h after tail vein administration (FIG. 10). The majority of the particles was cleared by the liver, while the levels of nanochains in the heart, lungs, and kidney were very low. Most importantly, vascular targeting of MPNC resulted in significant drug deposition in the brains of the glioma-bearing animals compared to negligible amounts in healthy brains.

Histological Evaluation

Using human PDX and rodent glioma models in mice, we have performed a series of detailed histological analyses to evaluate 1) the localization of MPNC particles at the brain-tumor interface in primary and invasive brain tumor sites, 2) the degree and topology of drug delivery upon application of the RF field, and 3) the anticancer effect of the effective delivery of different drugs to different cell subpopulations of the glioma tumors. FIG. 11 shows an example in a highly invasive human glioma model.

From the above description of the application, those skilled in the art will perceive improvements, changes and modifications. Such improvements, changes, and modifications are within the skill of those in the art and are intended to be covered by the appended claims. All patents, patent applications, and publication cited herein are incorporated by reference in their entirety.

Having described the invention, the following is claimed:

1. A method of forming a multi-component nanoconstruct, the method comprising:

suspending in a solution a plurality of unbound first nanoparticles having first functional chemical groups uniformly and symmetrically dispersed on the surfaces of the first nanoparticles and a plurality of unbound second nanoparticles having differing second functional chemical groups uniformly and symmetrically dispersed on the surface of the second nanoparticles, reacting the second functional chemical groups of the second nanoparticle with the first functional chemical groups of the at least two of first nanoparticles to link the at least two of first nanoparticles and the second nanoparticle and form linear nanochains that include three to five nanoparticles, wherein the reaction is arrested before the linear nanochain grows into a larger agglomerate, and separating the linear nanochains from the solution.

2. The method of claim 1, the nanoparticles having a diameter of about 1 nm to about 50 nm.

3. The method of claim 1, the nanochain having a length less than about 200 nm and a width of about 50 nm or less.

4. The method of claim 1, the nanochain comprising a first nanoparticle and a second particle that is formed of a different material than the first nanoparticle.

5. The method of claim 1, the nanoparticles comprising at least one of a metal nanoparticle, lipidic nanoparticle, polymer nanoparticle, liposome, or dendrimer.

6. The method of claim 1, wherein the first nanoparticle and the second nanoparticles include at least one iron oxide nanoparticle or gold nanoparticle.

7. The method of claim 1, further comprising functionalizing the linear nanochain with at least one targeting moiety.

8. The method of claim 1, further comprising reacting the linear nanochain with at least one liposome to form the nanoconstruct.

9. The method of claim 8, the liposome further comprising at least one of an imaging agent or therapeutic agent.

10. The method of claim 9, the therapeutic agent comprising an anti-cancer agent.

11. The method of claim 1, the nanochain comprising three or more metal nanoparticles, the nanochain being reacted with at least one of the a liposome, lipidic nanoparticle, or polymer nanoparticle, the liposome, lipidic nanoparticle, or polymer nanoparticle including an imaging agent or therapeutic agent, the metal nanoparticles when administered to a subject being responsive to an energy, from a remote source that is effective to release the imaging agent or therapeutic agent from the liposome, lipidic nanoparticle, or polymer nanoparticle.

12. A method of forming a multi-component nanoconstruct, the method comprising:

suspending in a solution a plurality of unbound first nanoparticles having first functional chemical groups uniformly and symmetrically dispersed on the surfaces of the first nanoparticles and a plurality of unbound second nanoparticles having differing second functional chemical groups uniformly and symmetrically dispersed on the surface of the second nanoparticles, activating the second functional chemical groups of the second nanoparticles so that they are reactive with the first functional chemical groups of the first nanoparticles, reacting the second functional chemical groups of the second nanoparticle with the first functional chemical groups of the at least two of first nanoparticles to link the at least two of first nanoparticles and the second nanoparticle and form linear nanochains that include three to five nanoparticles, wherein the reaction is arrested before the linear nanochain grows into an agglomerate, and separating the linear nanochains from the solution.

13. The method of claim 12, wherein the first functional chemical groups include amine groups tethered to the surface of the first nanoparticles and the second functional chemical groups include carboxyl groups tethered to the surface of the second nanoparticles.

14. The method of claim 12, wherein the second functional chemical groups are activated by reacting the second functional chemical groups with a carbodiimide in the solution.

15. The method of claim 12, wherein the first nanoparticle and the second nanoparticles include at least one iron oxide nanoparticle or gold nanoparticle.

16. The method of claim 12, further comprising functionalizing the linear nanochain with at least one targeting moiety.

17. The method of claim 12, further comprising reacting the linear nanochain with at least one liposome to form the nanoconstruct.

18. The method of claim 17, the liposome further comprising at least one of an imaging agent or therapeutic agent.

19. The method of claim 18, the therapeutic agent comprising an anti-cancer agent.

20. The method of claim 12, the nanochain comprising three or more metal nanoparticles, the nanochain being reacted with at least one of the a liposome, lipidic nanoparticle, or polymer nanoparticle, the liposome, lipidic nanoparticle, or polymer nanoparticle including an imaging agent or therapeutic agent, the metal nanoparticles when administered to a subject being responsive to an energy, from a remote source that is effective to release the imaging agent or therapeutic agent from the liposome, lipidic nanoparticle, or polymer nanoparticle.

21. The method of claim 12, wherein second functional chemical groups of the second nanoparticles are deactivated to arrest the reaction between the second functional chemical groups of the second nanoparticle with the first functional chemical groups.

22. A method of forming a multi-component nanoconstruct, the method comprising:

suspending in a solution a plurality of unbound first nanoparticles having first functional chemical groups uniformly and symmetrically dispersed on the surfaces of the first nanoparticles and a plurality of unbound second nanoparticles having differing second functional chemical groups uniformly and symmetrically dispersed on the surface of the second nanoparticles, wherein the plurality of first and second unbound nanoparticles form a stable suspension in an organic solvent, reacting the second functional chemical groups of the second nanoparticle with the first functional chemical groups of the at least two of first nanoparticles to link the at least two of first nanoparticles and the second nanoparticle and form linear nanochains that include three to five nanoparticles, wherein the reaction is arrested before the linear nanochain grows into an agglomerate, and separating the linear nanochains from the solution.

* * * * *